United States Patent [19]

Shah et al.

[11] Patent Number: 4,935,875
[45] Date of Patent: Jun. 19, 1990

[54] CHEMICAL ANALYZER

[75] Inventors: Ramesh M. Shah, Indianapolis, Ind.; Thomas H. Ridgway, Cincinnati, Ohio

[73] Assignee: Data Chem, Inc., Indianapolis, Ind.

[21] Appl. No.: 312,353

[22] Filed: Feb. 13, 1989

Related U.S. Application Data

[63] Continuation of Ser. No. 127,524, Dec. 2, 1987, abandoned, which is a continuation of Ser. No. 13,021, Feb. 10, 1987, abandoned, which is a continuation of Ser. No. 552,381, Nov. 16, 1983, abandoned.

[51] Int. Cl.$^5$ ............... G01J 3/42; G06F 15/02
[52] U.S. Cl. ..................... 364/497; 364/706; 364/709.01; 235/375; 235/462; 356/39; 356/300; 356/319
[58] Field of Search ............... 364/496–498, 364/464.01, 706, 709.11, 478; 356/39, 300, 326–334; 235/375, 462, 472, 456

[56] References Cited

U.S. PATENT DOCUMENTS

| | | | |
|---|---|---|---|
| 3,633,012 | 1/1972 | Wilhelmson et al. | 364/498 |
| 3,701,601 | 10/1972 | Plumpe, Jr. et al. | 364/498 X |
| 3,704,953 | 12/1972 | Carter et al. | 256/332 X |
| 3,868,499 | 2/1975 | Aaronson et al. | 356/326 X |
| 3,972,617 | 8/1976 | Shibata et al. | 364/498 X |
| 4,156,282 | 5/1979 | Olander, Jr. et al. | 364/709 |
| 4,218,746 | 8/1980 | Koshiishi | 364/497 X |
| 4,318,616 | 3/1982 | Chamran et al. | 356/334 X |
| 4,322,807 | 3/1982 | Chamran et al. | 364/498 |
| 4,323,773 | 4/1982 | Carpenter | 235/375 X |
| 4,330,210 | 5/1982 | Hashimoto et al. | 356/328 |
| 4,330,839 | 5/1982 | Miller et al. | 364/200 X |
| 4,357,673 | 11/1982 | Willis et al. | 364/575 X |
| 4,460,824 | 7/1984 | Kadogaki | 235/375 |
| 4,469,441 | 9/1984 | Bernier et al. | 356/334 X |
| 4,475,153 | 10/1984 | Kihara et al. | 364/145 |
| 4,479,197 | 10/1984 | Haag et al. | 364/900 |
| 4,481,412 | 11/1984 | Fields | 235/462 X |
| 4,528,623 | 7/1985 | Tachibana | 364/188 X |
| 4,588,880 | 5/1986 | Hesser | 364/478 X |
| 4,613,942 | 9/1986 | Chen | 364/478 X |
| 4,733,965 | 3/1988 | Inman, Jr. et al. | 364/498 X |

OTHER PUBLICATIONS

"Hewlett Packard Series 40 Advanced Calculators" Hewlett Packard Corp. Office, 3000 Hanover St., Palo Alto, Calif. 94304, Oct. 1983, pp. 1–32.
Hewlett Packard Measurement/Computation, *Electronic Instruments and Systems*, pp. 614–615, 1981.

Primary Examiner—Parshotam S. Lall
Assistant Examiner—Joseph L. Dixon
Attorney, Agent, or Firm—Frost & Jacobs

[57] ABSTRACT

An automatic chemical analyzer for the analysis of physiological samples. A scanning monochromatic spectrophotometer may be used to determine the absorbance of the sample under control of a central processing unit. Outputs from one of several ion selective electrodes may also be selected by the system. The information obtained from the measurements is stored in memory or ouputted to output devices. Information about the test parameters may be read from an optical bar code associated with the test kit for the particular chemical analysis.

8 Claims, 4 Drawing Sheets

CHEMICAL ANALYZER

This is a continuation of application Ser. No. 07/127,524, filed Dec. 2, 1987 which is a continuation of Ser. No. 07/013,021 filed Feb. 10, 1987 which is a continuation of Ser. No. 06/552,381 filed Dec. 16, 1983 now all abandoned.

SUMMARY OF THE INVENTION

The present invention is directed generally to a chemical analyzer, and more specifically to an analyzer for the automated chemical assay of blood, urine and cerebrospinal fluids, particularly in vitro blood chemistry, coagulation and electrolyte analyses. By determining the concentration of key chemical factors in these fluids, data relating to the pathological status of the patient may be obtained which leads to early diagnosis and treatment.

The chemical analyzer of the present invention is designed to perform the chemical analysis by measuring the optical absorbance of species or the reaction products of species in the clinical sample, or the chemical activity of species or their reaction product of the sample using ion selective microelectrodes. Both types of tests are under control of a central processing unit such as a digital computer and particularly a microprocessor which monitors the test results and provides display capability of the test results in the form of a visual, graphical or plotted display. For example, the results of a particular test may be plotted as a bar graph or histogram. Similarly, the test data produced by the chemical analyzer may be integrated with other patient information stored in a host computer such as medical history or billing information.

The optical tests performed by the chemical analyzer are based on the ability of a particular chemical involved in the sample to combine with other chemicals, specifically reagents provided with the usual clinical test kit, to form a compound which absorbs light of a specific wavelength, usually in the ultraviolet or visible region. This chemical compound has a characteristic color, referred to as a chromagen.

The optical test section of the present invention includes a dual beam scanning monochromatic spectrophotometer which is used to measure the amount of light absorbed by the sample. The specific measurement parameters for the particular test such as temperature, time, and wavelength are set precisely under computer control. The test results may then be communicated to an appropriate output device.

For ion selective electrode experiments, the particular electrode sensitive to a species and a reference electrode are immersed in the sample and a potential measurement taken. This information may be stored within the computer memory space, or outputted for display to an appropriate display device.

The specific test parameters are inputted to the system by reading an optical bar code on the reagent package supplied for each test. The bar code is read from the reagent package by means of a wand, the data being under control of the central processing unit within the analyzer. For example, this bar code may provide information relating to the reagent, lot number, expiration date of the reagent, the type of experiment to be performed (i.e. optical or ion selective electrode), information regarding the calibration curve for the test, the clinical acceptable range, the units, the reagent number, quantity of reagent used, etc. In the case of an optical experiment, the specific wavelength required may be specified in the bar code, while in the case of an ion selective electrode experiment, the specific electrode number may be provided. With this approach, all of the information relating to a new experiment can be incorporated into the bar code, without the need to reprogram the chemical analyzer itself.

The specific circuitry and processing used in the present invention will become apparent from the detailed description which follows.

DETAILED DESCRIPTION

Figure 1:
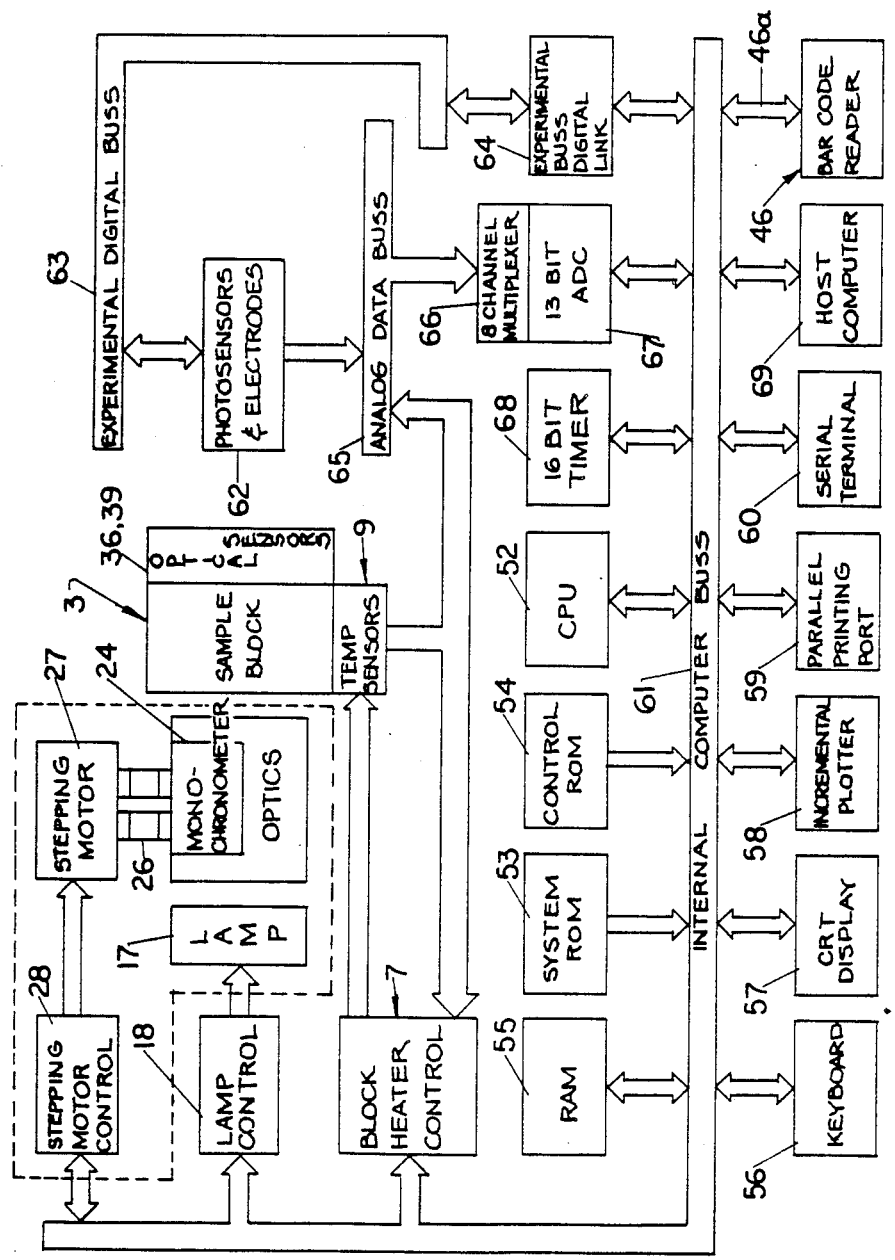
FIG. 1 is a block diagram of the chemical analyzer of the present invention.
Figure 2:
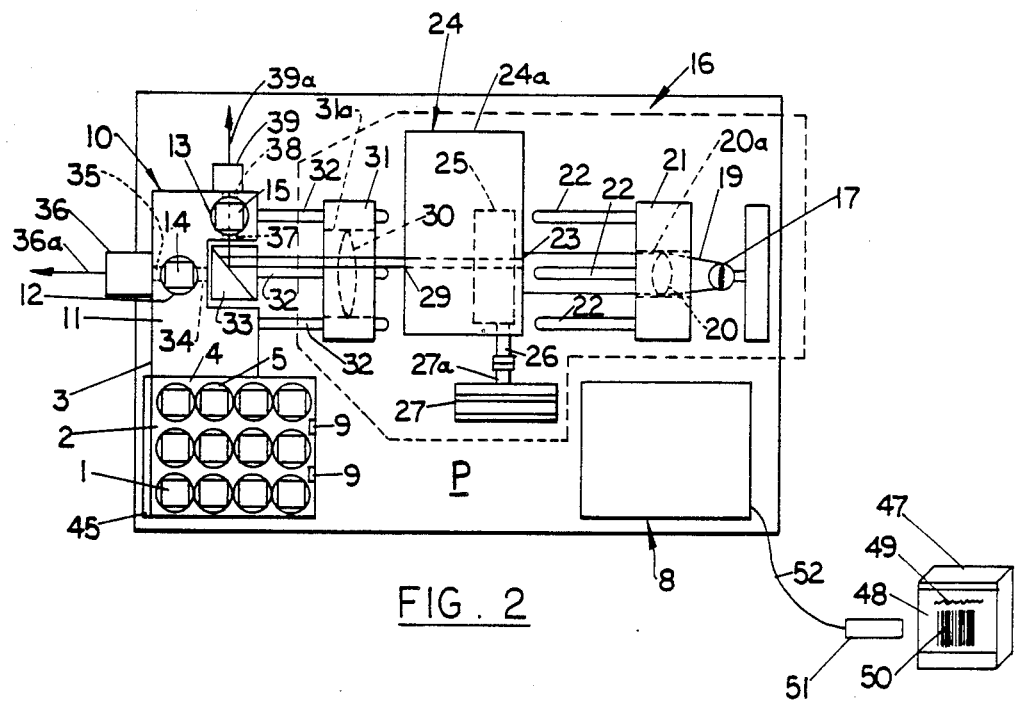
FIG. 2 is a diagrammatic top plan view of a portion of the chemical analyzer of the present invention.
Figure 3:
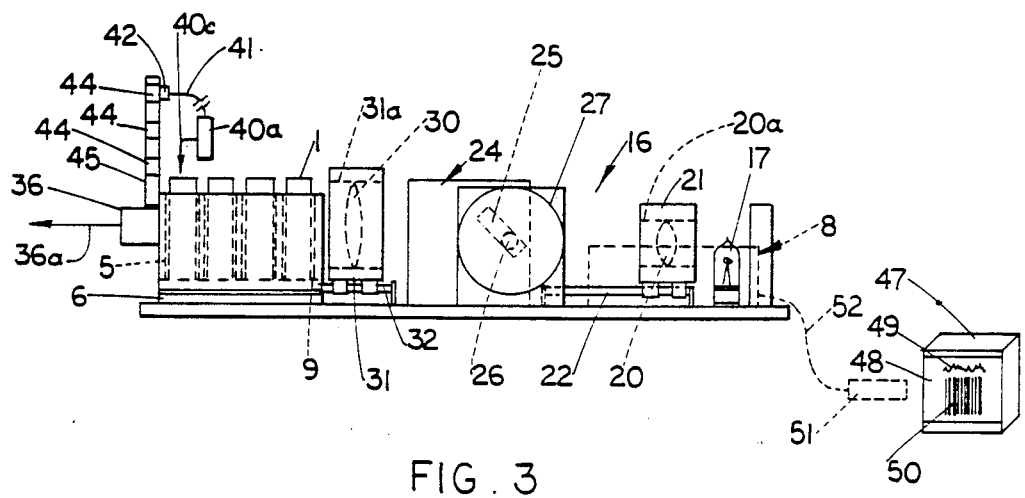
FIG. 3 is a diagrammatic side elevational view of a portion of the chemical analyzer of the present invention.

The block diagram of the chemical analyzer of the present invention is illustrated in FIG. 1, and the arrangement of the mechanical and electrical components of the present invention is illustrated, in FIG. 2 and FIG. 3. It will be understood that certain non-critical components of the chemical analyzer unnecessary to the understanding of its construction and operation of the analyzer have been deleted for clarity. Furthermore, for purposes of an exemplary showing the various mechanical and electrical components are illustrated as being mounted on a generally rectangular base plate P.

The physiological fluid, such as blood, urine or cerebrospinal fluid, to be anyalyzed is placed in an optical cuvette or precision test tube 1. The appropriate reagent or reagents necessary to carry out the particular chemical test procedure are also placed in the cuvette and mixed or incubated as required.

In order to maintain the test sample at the appropriate temperature during the analysis, one or more cuvettes 1 may be placed in an incubator 2 which forms part of a heated sample block 3.

As best illustrated in FIG. 2 and FIG. 3, sample block 3 comprises a solid block 4 of aluminum or other heat conducting material rigidly mounted to base P and which contains twelve vertically oriented side-by-side bores or receptacles of square cross section, one of which is shown at 5 arranged in three rows, with four receptacles in each row. Each of bores 5 is dimensioned to accept a cuvette 1 and hold the cuvette in an upright position during incubation. Although the incubator 2 described in connection with the present invention is provided with twelve cuvette-accepting bores 5, it will be understood that any number of such bores or receptacles may be provided.

Means are also provided for maintaining incubator 2 (and the cuvettes retained therein) at a constant temperature. As illustrated in FIG. 3, this heating means includes an electrically operated heating element 6 secured to the lower portion of incubator 2 so as to underline the bottom of bores 5. In the preferred embodiment illustrated, heater 6 comprises a number of resistive heating elements embedded in a flexible silicon rubber so as to form a pad-like heater. Heater 6 is secured by a suitable adhesive or the like in heat exchange relationship with metallic block 4 so as to uniformly heat the block, and the sample containing cuvettes deposited therein.

Electric current is supplied to heater 6 by means of a block heater control, shown generally at 7 in FIG. 1, as is well known in the art. The control 7 which may be electronic in nature, may be included as part of the electronics associated with the chemical analyzer and indicated generally at 8 in FIG. 2.

The temperature of the heat conducting block comprising incubator 2 is monitored by means of two temperature sensors 9 embedded in block 3, in order to maintain the temperature of the incubator at a constant temperature, preferably 37 C.±0.5 C. This close temperature control provides the proper temperature environment for incubation of the test sample, and is particularly important in blood, urine and cerebrospinal fluid in vitro chemistry analysis, notably with respect to coaggulation or electrolyte analysis, which may be particularly temperature dependent. It will be observed that one of temperature sensors 9 continuously monitors the temperature of the sample block 3 while the other temperature sensor operates to cause block heater control 7 to disable heater 6 in the event the temperature of the sample block reaches a predetermined limit, e.g. 38 C.

The remaining portion of sample block 3 comprises the sample test station, indicated generally at 10. Test station 10 is formed from a block 11 of heat conducting material, such as aluminum, and shares a portion of heater 6, so that block 11 is also maintained at a relatively constant temperature of about 37 C.±0.5 C. If desired, block 11 may be formed as an integral part of block 4, both of which are rigidly secured to base plate P.

Block 11 comprising test station 10 contains a pair of spaced vertically extending bores 12 and 13, similar to bores 5 in incubator 2, for accepting and holding a sample cuvette 14 and reference cuvette 15, respectively. That is, bore 12 forms a sample well into which the sample cuvette is manually placed, while bore 13 forms a reference well into which a reference cuvette, either with or without reagent, is manually deposited. These wells are utilized in connection with the optical analysis section of the chemical analyzer as will be explained in more detail hereinafter.

As noted briefly hereinabove, one of the principles used in the chemical analyzer of the present invention is the ability of certain chemical substances to absorb a specific band or bands of light in the ultraviolet or visible regions of the spectrum. Thus, the chemical composition of the substance may be defined by a characteristic color, based on the ability of the substance to absorb light of specific wavelengths or color. Ideally, the concentration of the substance is proportional to the depth of the characteristic color, as governed by the absorbance of certain bands of light. These principles are well known in blood, urine and cerebrospinal fluid analysis.

In many types of chemical analysis associated with blood, urine or cerebrospinal fluids, it is necessary to react the sample with exact amounts of certain specified reagents to form a chromogen. The optical chemical analysis section of the chemical analyzer of the present invention is designed to measure the amount of light that the particular resultant chromogen absorbs.

In the preferred embodiment of the chemical analyzer of the present invention illustrated in FIG. 2 and FIG. 3, the optical analysis section includes a dual beam scanning monochromatic spectrophotometer, illustrated generally at 16 in FIG. 2 as rigidly mounted to base plate P, which is designed to measure the amount of light that the chromogen absorbs, i.e. its color intensity. The monochromatic spectrophotometer 16 operates by passing a beam of filtered light through an optical cuvette which contains the chromogen. The beam of filtered light is then projected on a photodetector or photosensor, which produces an electrical current corresponding to the amount of impinging light. This current is then used to provide a measure of the absorbance of the sample in the cuvette.

In the preferred embodiment illustrated, the light source associated with the spectrophotometer comprises a tungsten filament incandescent lamp 17 which produces usuable light energy in the ultraviolet and visible ranges, principally 300–780 nm. The lamp 17 may be turned on or off by appropriate control signals by means of a lamp control 18 (see FIG. 1) as is well known in the art. The voltage applied to lamp 17 by lamp control 18 is carefully controlled through a conventional well regulated power supply or the like so that the intensity of the lamp is substantially constant.

The light rays, indicated generally at 19, emitted from lamp 17 pass through a prefocus or collimating lens 20 which is mounted horizontally oriented base 20a in a lens mounting block 21. Mounting block 21 is slidably supported on three horizontal mounting rails 22 secured to plate P so as to be slidable toward and away from lamp 17. This enables the focus of prefocus lens 20 to be manually adjusted.

The light rays leaving prefocus lens 20 pass through a narrow vertically disposed entrance slit 23 in the side of box-like casing 24a of the monochronometer 24.

Monochronometer 24 includes a defraction grating 25 mounted within the monochronometer 24 by means of a control shaft 26 which rotatably extends through the end of the monochronometer housing 24a. It will be understood that monochronometer housing 24a is generally light-tight. The opposite end of control shaft 6 is connected to a drive shaft 27a of a multiple position stepping motor 27, which is used to control the angular position of the defraction grating 25. Angle input information to stepping motor 27 is provided by a stepping motor control 28 (which may generally comprise part of electronics 8), as is well known in the art. Consequently, by providing the properly encoded digital input signals to stepping motor control 28 as will be described hereinafter, the stepping motor, and consequently the defraction grating 25, may be moved to any desired angular position with respect to the incoming light beam. In the specific embodiment illustrated in the present invention, the monochronometer is usable over the ultraviolet range of 340–400 nm and the visible range of 400–780 nm. Furthermore, for purposes of exemplary showing, it will be understood that monochronometer 24 may comprise a conventional monochronometer unit, such as Model SMC1-03 manufactured by PTR Optics.

The monochromatic light leaving defraction grating 25 passes through a narrow vertically disposed exit slit 29 generally in-line with entrance slit 23 and a focusing lens 30 which serves to collimate the light beam. Focusing lens 30 is mounted in a horizontally extending base 31a formed in a lens mounting block 31 which is also slidably mounted on three parallel 32 horizontally extending rails secured to base plate P and similar in construction to rails 22, thereby permitting manual focusing of lens 30. This adjustment would normally be made by the manufacturer, and not by the user.

The collimated light from focusing lens 30 impinges on an optical beam splitter 33 mounted in close proximity to sample test station 10. A portion of the collimated beam is directed by the beam splitter toward sample well 12, while the remainder of the collimated beam is deflected toward reference well 13. The portion of the beam directed toward the sample well passes through an opening 34 in block 11 which communicates with sample well 12. After passing through sample cuvette 14, the monochromatic light beam exits sample well 12 through an opening 35 in block 11, and impinges on sample photosensor or photodiode 36. As will be explained in more detail hereinafter in connection with the electronic schematic diagram illustrated in FIG. 4, the amount of current produced by sample diode 36 an output line 36a provides a measure of the absorbance of the chromogen contained in sample cuvette 14 at the particular monochromatic wavelength produced by monochronometer 24.

The monochromatic collimated light beam deflected toward reference well 13 passes through an opening 37 communicating with reference well 13 through block 11. After passing through the reference well, the light beam exits sample test station 10 by means of an exit opening 38 and impinges on reference photodiode or photosensor 39. As will be explained in more detail hereinafter in connection with the electronic schematic diagram of FIG. 4, the amount of current produced by reference photodiode 39 on output line 39a is used in conjunction with the amount of current produced by sample photodiode 36 to calculate the absorbance of the sample material within sample cuvette 14.

It will be understood that in some instances, it may be necessary to place a reference cuvette 15 within sample well 12 in order to calibrate the optical path for specific chemical tests. In other types of tests, the material forming the reference cuvette will have no significant effect on the reference optical beam, and thus may be eliminated.

The chemical analyzer of the present invention is also provided with a plurality of ion selective electrodes, one of which is illustrated diagrammatically at 40a in FIG. 3, for performing other chemical analyses. The construction and operation of such electrodes is well known in the art, and need not be described in detail. In the present invention, each electrode 40a is connected by means of a wire or cable 41 to a plug 42 which mates with one off several jacks 44 mounted on a jack panel 45. It will be understood that jack panel 45 may be provided with a plurality of jacks 44, each adapted to mate with a connecting plug 42 of an associated ion selective electrode 40a. In the embodiment illustrated, jack panel 45 is vertically mounted vertically adjacent incubator block 2 so that one or more of the electrodes may be inserted into the test solutions contained within the cuvettes 1 mounted in the incubator as indicated diagrammatically by arrow 40c in FIG. 3. There is also one reference electrode 40b (see FIG. 4) which must be present in the sample in conjunction with any individual sensor electrode 40a. The specific type of ion selected electrode will be chosen for the particular chemical analysis to be performed as is well known in the art.

An important part of the present invention is the bar code reader illustrated generally at 46 in FIG. 1. The bar code reader 46 is used in conjunction with a wand to be described hereinafter to read a 28 character bar code supplied with the reagent container. This bar code contains all of the information about the reagent and the particular test being performed. As illustrated in FIG. 2 and FIG. 3, for example, the reagent container 47 supplied as part of a test kit for a particular chemical test is provided with a label 48 bearing printed indicia 49 describing the type of test, type of reagent, etc., as well as a conventional bar code 50. The bar code 50 encodes information relative to the reagent and test such as the lot number and expiration date of the reagent, the type of experiment to be performed (i.e. optical or ion selective electrode), the calibration curve for the test, the clinical acceptable range, the units, the reagent number, quantity of reagent to use, etc. In the case of an optical experiment, the wavelength may be specified in the bar code, and in the case of an ion selective electrode experiment, the channel number or electrode number may be given (i.e., which of the several electrodes 40 should be immersed in the sample solution). With this approach, all of the information relating to a new experiment can be incorporated into the bar code, without the need to reprogram the chemical analyzer itself.

The bar code is read by means of a wand 51 which may be a Hewlett Packard Type HEDS-3050 and, which is connected to electronics 8 by means of a suitable cable 52. For purposes of an exemplary showing, bar code reader 46 may comprise a Hewlett Packard type HEDS-1050 bar code reader which produces suitable data on line 46a (see FIG. 1) according to the information read from the bar code 50. The specific utilization of the bar code reader in connection with the chemical analyzer of the present invention will be described in more detail hereinafter.

The block diagram summarizing the signal processing components of the present invention is illustrated in FIG. 1, where the elements similar to those previously described have been similarly designated.

System operation is controlled by a data processor comprising a central processing unit or CPU 52 which may be any suitable type of digital computer, such as a 6809 or other microprocessor based system. The control program, particularly the processing for the chemistry experiments, is stored in system ROM 53 and control ROM 54, which may be implemented as "firmware" in a suitable integrated circuit chip. A suitable program listing for this purpose is described in Appendix I hereto. Read/write memory is supplied by RAM 55.

Information is inputted to processor 52 by means of a conventional keyboard 56, associated with host computer 69, and output information may be displayed by means of a CRT display 57, incremental plotter 58, or the like. An additional parallel printer port 59 and a serial terminal 60 are also provided.

The foregoing processing elements communicate by means of an internal computer buss 61, as is well known in the art. In addition, communication is provided through the internal computer buss 61 with bar code reader 46, block heater control 7, lamp control 18 and stepping motor control 28, as will be described in more detail hereinafter.

The photosensors 36 and 39 associated with monochronometer 24 and the ion selective electrodes 44, both designated by block 62 in FIG. 1, communicate with internal computer buss 61 through experimental digital buss 63 and experimental buss digital link 64. That is, as will become apparent from the detailed description which follows, the information obtained from the monochronometer and ion selective electrodes is converted to a digital format for use by CPU 52 in conjunction with its operating program. Digital link 64 may be implemented by means of tristate gates which isolate the experimental digital buss from the internal computer buss.

The analog information produced by the photosensors and electrodes comprising block 62 communicates with the internal computer buss 61 as will be explained hereinafter through an analog data buss 65, an eight channel multiplexer 66, and a thirteen bit analog/digital converter 67. The A/D converter 67 permits the analog voltages to be presented on the internal computer digital buss as is well known in the art. The analog information from block heater control 7 and temperature sensors 9 also communicate with the system through the analog data buss 65.

There is also associated with the chemical analyzer of the present invention three sixteen bit timers 68 which control some of the timing functions associated with the experiments, such as the prothrombin coagulation time analysis experiment.

The chemical analyzer of the present invention may also communicate through internal computer buss 61 with an external host computer 69 so as to integrate the chemical analysis information with other patient information. For example, the results of specific in vitro blood, urine and cerebrospinal fluid chemistry or electrolyte analyses may be integrated with the patient's medical history or billing and insurance information stored in the host computer. Likewise, data associated with the patient and relative to the particular diagnostic test such as age, weight, height, sex, and so forth, may be called from the host computer data base management system and used as input information to the diagnostic test being performed. The host computer 69 may also be used to control the overall operation of the chemical analyzer according to the specific instructions contained in the message code from the host computer, such as commands for setting the monochronometer 24 to a particular wavelength, interrogating the temperature of sample block 3, reading the voltage produced by a particular ion selective electrode, etc. Examples of each of these functions will be given in greater detail hereinafter.

Figure 4:
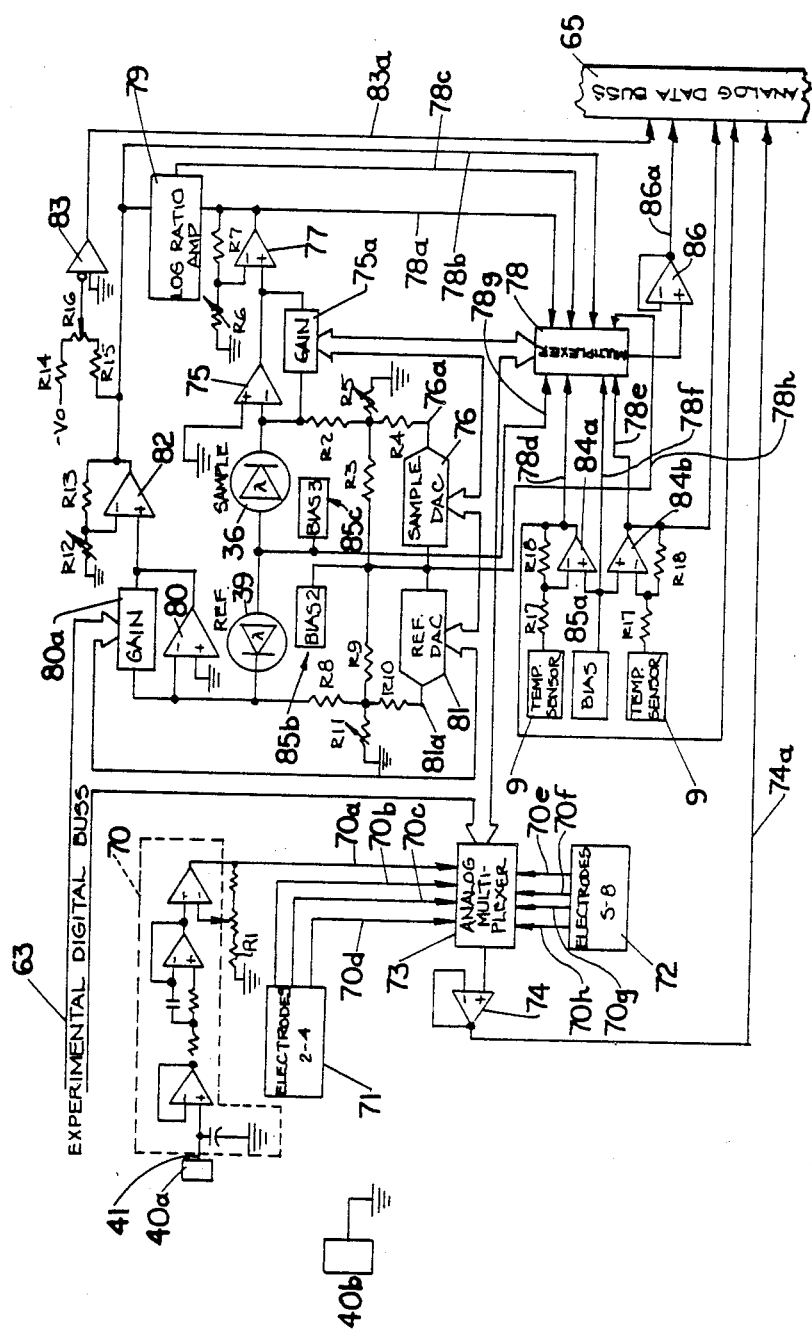
FIG. 4 is a schematic diagram of a portion of the electronic processing circuitry of the present invention.

The electronic interface associated with the photosensor and electrode section 62 is illustrated schematically in FIG. 4. A high impedance electrometer amplifier, shown generally at 70 in FIG. 4, is connected to each of the ion selective electrodes 40a. It will be understood that in connection with the described embodiment of the present invention, there are eight ion selective electrodes, each having its own high impedance amplifier 70. It will be further understood that the second to fourth electrodes and the amplifiers associated therewith are represented by the block designated 71, while the fifth through eighth electrodes and the amplifiers associated therewith are designated by block 72. A reference electrode 40b is connected to analog signal ground. The gain of each amplifier 70 may be adjusted by variable resistor R1 in order to calibrate each of the ion selective electrode channels 1-8. This calibration is made during manufacture.

Each of the high impedance amplifier channel outputs 70a-70h is connected to an analog input of analog multiplexer 73. The output of multiplexer 73 is connected through buffer amplifier 74 to analog data busss 65. The selection of the eight ion selective electrode channels by means of analog multiplexer 73 is under the control of digital command signals produced by CPU 52 appearing on experimental digital busss 63. Consequently, by the appropriate digital input code to analog multiplexer 73, any one of the ion selective electrode channels may be read and this analog information outputted on analog data busss 65 via output line 74a.

As illustrated in FIG. 4, sample photodiode 36 is reversed biased to approximately −2.48 volts via bias voltage source 85c, and the current output of the photodiode converted to a voltage by means of operational amplifier 75. The feedback impedance 75a for operational amplifier 75 (designated "gain" in FIG. 4), is digitally controlled by CPU 52 through experimental digital buss 63. Consequently, the gain of operational amplifier 75 may be adjusted under computer control.

An active network is also provided to suppress or compensate for the photodiode dark current. This network includes a fixed resistor R2 connected between the inverting input of amplifier 75 and the junction of resistors R3, R4 and variable resistor R5. The remaining terminal of resistor R5 is connected to ground. The remaining terminal of resistor R4 is connected to the output of sample digital-to-analog converter ("sample DAC") 76, which is responsive to digital command signals on the experimental digital buss 63 from CPU 52. The remaining terminal of R3 is biased to approximately −5.00 V by bias voltage source 85b, which also provides the reference voltage for sample D/A connector 76. Consequently, the voltage produced on output line 76a by sample D/A converter 76 is under control of CPU 52 and operates to suppress the dark current for sample photodiode 36 as will be described in more detail hereinafter.

The output of amplifier 75 is connected to the non-inverting input of amplifier 77. The inverting input of amplifier 77 is connected to ground through variable resistor R6. The gain of amplifier 77 is determined by feedback resistor R7. The output of amplifier 77 forms one of the inputs on line 78a to an analog multiplexer 78, and is also connected to the input of log ratio amplifier 79.

A somewhat similar arrangment is used for biasing and dark current suppression of reference photodiode 39. This diode is reverse biased to approximately −2.48 volts. The current from the diode is converted to a voltage by means of amplifier 80, the gain of which may be adjusted by varying the value of feedback impedance 80a (marked "gain" in FIG. 4) under control of digital signals produced by CPU 52 on experimental digital buss 63. The dark current of reference photodiode 39 is suppressed by the network comprising resistors R8-R11, and reference digital-to-analog converter 81 ("Ref. DAC"). In a manner similar to that previously described, appropriate digital signals produced by CPU 52 on experimental digital buss 63 will cause reference D/A converter 81 to produce a voltage on output line 81a to suppress the dark current produced by reference photodiode 39.

The output of amplifier 80 is connected to the non-inverting input of amplifier 82, while the inverting input of this amplifier is connected to ground through variable resistor R12. The nominal gain of amplifier 82 may be set by feedback resistor R13.

The output of amplifier 82 is connected to log ratio amplifier 79, and also forms one input 78b to analog multiplexer 78. The output from amplifier 82 is also supplied as an input to a voltage comparator formed by amplifier 83. The trigger point of the comparator may be set by the voltage divider formed by fixed resistors R14 and R15, and variable resistor R16. The digital output from the comparator is applied to analog data buss 65 on line 83a.

It will be understood that the gain and bias conditions on sample photodiode 36 and reference photodiode 39 may be calibrated by adjustment of variable resistors R5, R6, R11, R12 and R15 to compensate for the sensitivity and dark current differences in various photodiodes.

Log ratio amplifier 79 uses the voltages produced by sample and reference photodiodes 36 and 39, respectively present on lines 78a and 78b, to calculate the absorbance of the chromogen under test. As is well known the absorbance is defined as the products of the extinction coefficient, path length and concentration associated with a particular solution. This may also be defined as the logarithm of the ratio of the sample intensity to the reference intensity. In the present invention, log ratio amplifier 79 operates to divide the value of the voltage produced by sample photodiode 36 by the value of the voltage produced by reference photodiode 39, and takes the logarithm of this ratio to calculate the absorbance. This absorbance value is provided as an analog input to multiplexer 78 on line 78C.

The output current from each of the temperature sensors 9 (which is representative of the actual temperature of sample block 3) is converted to a voltage by means of an associated amplifier 84 and resistors R17 and R18, and the resulting voltages applied as inputs 78d and 78e, respectively, to analog multiplexer 78 and to analog data buss 65. The bias voltage for the temperature sensors 9 is produced by bias voltage source producing means 85a and applied to the non-inverting input of amplifiers 84a and 84b, and as an analog input 78f to multiplexer 78.

The photodiode bias voltage at the anodes of photodiodes 36 and 39 is provided as an input to analog multiplexer 78 on line 78g for mounting the bias conditions of the the photodiodes. Similarly, the bias voltage at the junction of resistors R3 and R9 is supplied as an input to multiplexer 78 on line 78h.

The output of analog multiplexer 78 is connected through voltage follower amplifier 86 to analog data buss 65 via line 816a.

It will be observed that any of the inputs 78a–78h to analog multiplexer 78 may be selected by appropriate digital commands from CPU 52 communicated on experimental digital buss 63. Consequently, CPU 52 may be used to select either of the temperature sensor outputs or their bias voltage, either of the sample or reference photodiode outputs or their bias or dark current suspension reference voltages, or the absorbance value produced on output line 78C of log ratio amplifier 79.

As noted hereinabove, the operation of the chemical analyzer of the present invention is under control of CPU 52 and host computer 69. An exemplary program which may be used to control the processing associated with the chemical analyzer is summarized in the flow diagram of FIG. 5 and is set forth in detail in Appendix I. This program is particularly adapted for use with a 6809 based system running under the OS9 operating system. It will be understood that this program may be implemented as "firmware" in system ROM 53 or control ROM 54. Each of the program instructions is stored at a memory location between 0000 and FFFF (expressed in hexadecimal notation. For example, most of the application programs are located between about 0000 and 1FFFF. RAM is located at about 2000-27FF and 8000-8800, with system RAM at about F800-F8FF. I/O is located at about 3000-4800.

Figure 5:
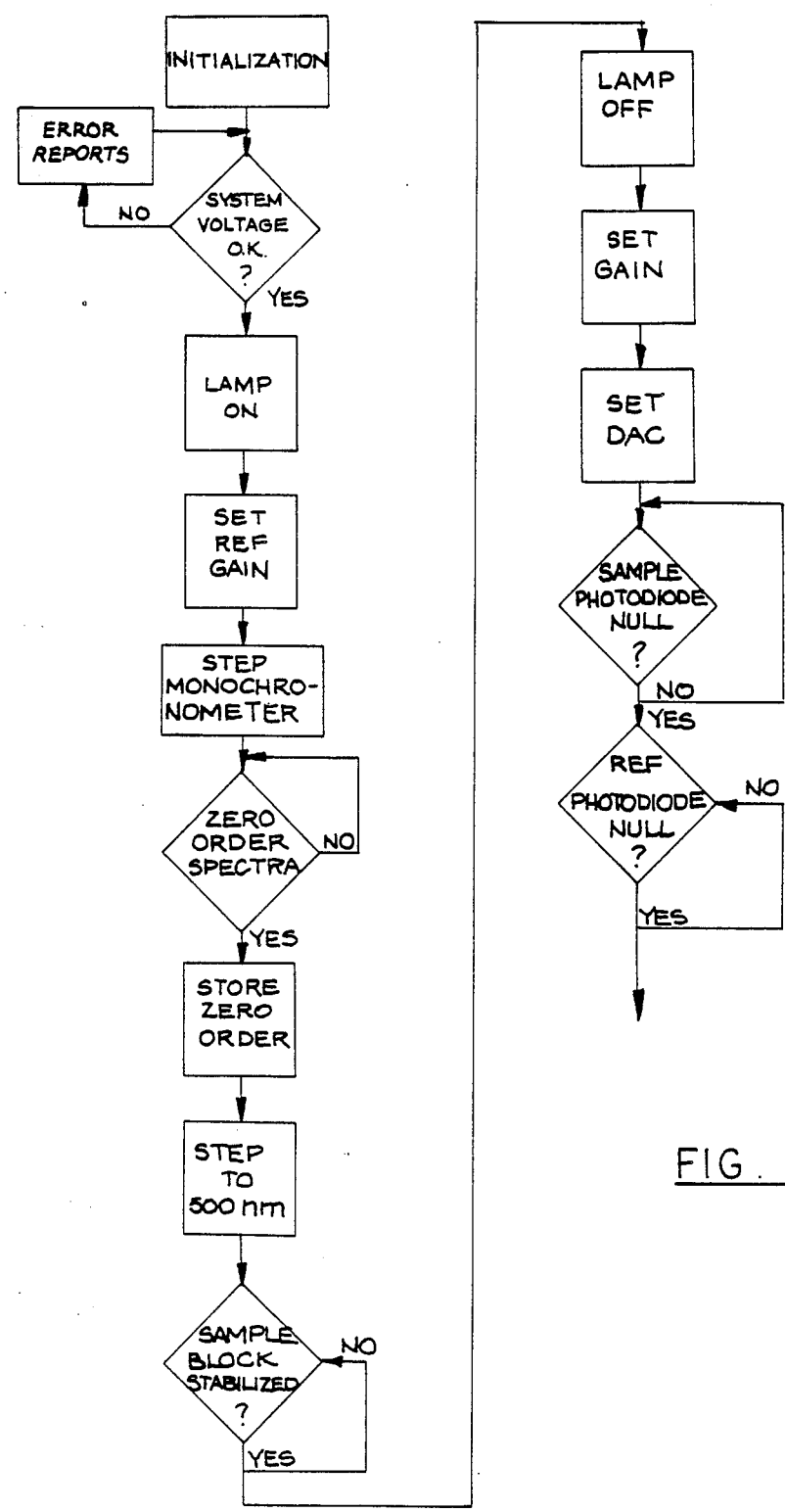
FIG. 5 is a flow diagram of a portion of the processing of the present invention.

With reference to FIG. 5, the system processing first proceeds through an initialization sequence in which certain system parameters are verified and pointers set (see, e.g. memory locations 0F80-0FF00). A check is then made to determine whether or not all system supply voltages and bias voltages are within tolerance utilizing the instructions located in memory at about 0CC6–OCEA in the exemplary program described in Appendix I. Next, incandescent lamp 17 is turned on by means of lamp control 18. For example, a digital "1" produced by CPU 52 will turn the lamp on, while a digital "0" produced by the CPU will turn the lamp off.

CPU 52 then produces signals on experimental digital buss 63 which changes the gain of reference photodiode amplifier 80 via impedance 80a until the lowest sensitivity or output voltage on line 78b is obtained.

CPU 52 then causes stepping motor control 28 to rotate defraction grating 25 by means of stepping motor 27 toward the lower wavelengths. At a particular angle, as measured between the defraction grating and the incident light beam from entrance slit 23, the grating in effect acts as a mirror, reflecting essentially all of the incident light toward exit slit 29. This angle is defined as the zero order angle, i.e. a position in the monochrometer spectra in which an intense spectral line is produced. When this point is reached, there is a sudden voltage increase from amplifier 82 which is applied to the voltage comparator formed by amplifier 83. This causes the output of amplifier 83 to change state and apply a signal or output line 83a to analog data buss 65. The position of stepping motor 27 when this sudden intensity increase occurs is stored in RAM 55 as the zero order spectral line. This provides a basepoint from which angular increments of monochronometer 24 may be measured. Consequently, any other wavelength may be unambiguously located relative to this zero order position of the defraction grating 25. The instructions for this processing are located in memory locations of about 0D13-0D64, as shown in Appendix I.

The system then causes stepping motor 27 to rotate the defraction grating 25 to the angular position corresponding to 500 nm. The angular position associated with this wavelength may be stored as a discrete number of stepper motor steps in control ROM 54, for example. This processing is defined by the program instructions stored in memory locations 0C5D-0CC6.

The processing then enters a loop waiting for the temperature of the sample block 3 to stabilize at 37C±0.5C, as monotored by temperature sensors 9 (memory locations 08E8-0900). It will be observed, as illustrated diagrammatically in FIG. 1 and FIG. 2, that the optical sensors comprising sample photodiode 36 and reference photodiode 39 are physically connected to and in heat exchange relationship with sample block 3 so that their temperature remains constant. This helps to stabilize the dark current of the photodiodes, and permits supervision of the dark current as described hereinabove.

When the sample block temperature has stabilized, lamp 17 is turned off and the gain of sample photodiode amplifier 75 and reference photodiode amplifier 80 adjusted via feedback impedances 75a and 80a to the highest sensitivity by appropriate digital commands on experimental digital buss 63 from CPU 52. The output voltages from sample D/A converter 76 on line 76a and reference D/A converter 81 on line 81a are set to approximately half-scale by appropriate digital signals on experimental digital buss 63. The output voltage from amplifier 77 on line 78a representing the dark current produced by sample photodiode 36 is selected by multiplexer 78 and applied to analog data buss 65. This voltage is then selected by eight channel multiplexer 66, converted to a digital voltage by A/D converter 67, and applied to internal computer buss 61. The voltage produced on line 76 by sample D/A converter 76 is then adjusted by appropriate commands on the experimental digital lines 63 until the value of the dark current-produced voltage on line 78a is less than about three millivolts. This thus serves to null or compensate for the dark current produced by the sample photodiode (see memory locations 0D13-0D3B). Since the photodiode is maintained at a relatively constant temperature, this dark current value will remain substantially constant.

A similar procedure is followed in connection with reference photodiode 39 in order to adjust reference D/A converter 81 to compensate for or null the reference dark current (see memory locations 0D3C-0D6i3). The resulting settings of the reference and sample D/A converters resulting in minimum dark current are stored in RAM 55.

Following these calibration checks, the system is ready to perform a desired chemical analysis. This may be accomplished, for example, by a prompt to host computer 69 to indicate that the system is ready for operation (see memory locations 0B97-0BB0).

Each possible command from host computer 69 is in the form of a message comprising a string of characters. The first character of the message comprises the destination code, i.e. the particular output device. The remainder of the command represents an instruction or data followed by an end of message character. For example, the particular destination code may direct certain instructions or data to CRT display 57, incremental plotter 58 or the chemical analyzer of the present invention (see, e.g., the instructions defined by memory locations 1802-1B20). In the exemplary implementation of the present invention, several possible instruction codes are utlized as further described in the exemplary program listing set forth in Appendix I.

For example, the instruction "T" queries the temperature of sample block 3. Consequently, an appropriate digital code is produced by CPU 52 on experimental digital buss 63 which selects, through multiplexer 78, the voltage produced by either of temperature sensors 9. This voltage is directed to analog data buss 65, converted to a digital signal by A/D converter 67, and communicated to CPU 52. Hence, the system may respond by a reply on CRT display 57 that the temperature of the block is, e.g. 3701*, i.e. 37.01C. This operation is controlled by the instructions at memory location 0BB1-0BC0 in Appendix I.

Another command is "L 0,:", which turns lamp 17 off, or "L 1,:", which turns the lamp off (see memory locations 0D76-0D7E).

The photodiode dark current null routine described hereinabove, may be initiated by the command "N", as defined by the instructions stored in memory locations 0D13-0D63.

The monochronometer 24 may be positioned at a new wavelength by means of the command "W", followed by a stop wavelength value. In other words, the command "W540", for example, directs CPU 52 to produce appropriate signals on internal computer buss 61 to cause stepping motor control 28 to rotate the defraction grating 25 a calculated number of steps from the current position described hereinabove corresponding to a final wavelength of 540 nm (see memory locations 0A30-0A61).

The spectra of a sample may be scanned by the "F" command followed by a stop wavelength value. As an example "F 760" would cause the monochronometer to scan the wavelength from its present position to 760 nm in steps of approximately 1 nm. Following execution of each step of the scan, an absorption reading is taken. This is accomplished by causing multiplexer 78 through appropriate signals on experimental data buss 63 to select the analog output on line 78a from log ratio amplifier 79, and apply this voltage to analog data buss 65. This voltage is then converted to a digital signal, and routed to the appropriate output device for displaying or printing the absorbance value at that particular wavelength. The system response, as determined by the voltage produced by log ratio amplifier 79 may be, e.g. 2136*, representing a reading of 2.136 absorbance units. The scan will continue with the absorbance being provided for every step of the monochronometer until the stop wavelength is reached. This value can then form part of the diagnostic report associated with the chemical analysis. This processing is defined by the instructions in memory locations 0A7A-0AD4.

A more involved command involving the monochronometer 24 is represented by "0", followed by the monochronometer wavelength and delay in tenths of a second. For example, the command "0 462, 300:" directs the system to move the monochronometer to 462 nm, wait 30 seconds, and then take an absorbance reading as described hereinabove. The time duration is determined by 16 bit timer 68 under control of CPU 52. This processing is defined by memory locations 0CEA-0CF2.

For an ion selective electrode experiment, after one or more of the electrodes 44 have been placed in the sample cuvette, the command "I 3:" is entered. This causes the system processing to select via analog multiplexer 73 the channel associated with electrode number 3, i.e. the signal on line 70C, for example, and place that voltage on the analog data buss 65. This voltage is then converted to a digital signal, and displayed on one of the output devices in an appropriate format (see, e.g., memory locations 0C24-0C33).

The chemical analyzer of the present invention also includes the capability to measure prothrombine coagulation time. As is well known, this test measures the time necessary for coaggulation to occur in an in vitro blood test sample. In the processing of the present invention, the test sample is inserted in sample well 12, and the command "N:" entered. This causes the system to step monochronometer 24 to a particular wavelength and start the timing of timer 68. The output from log ratio amplifier 79 on line 78C is then selected by analog multiplexer 78 and applied to analog data busss 65. This value is converted to a digital signal by A/D converter 67 and monitored by CPU 52 for a sudden decrease in output intensity. This sudden decrease in intensity or drop in light transmitted marks the prothrobine time. At this point, the elapsed time associated with timer 68 is read, and the time transmitted to the appropriate output port. For example, a particular in vitro blood sample, the system will respond with an output such as "P97", indicating a prothrombin time of 9.7 seconds. These steps can be carried out using the processing defined by memory locations 0C3A-0C57 in Appendix I.

The command "R:" inputs information from bar code reactor 46. This instruction causes information contained in the bar code to be stored in RAM 55 for use during the diagnostic test procedures (see, e.g., memory locations 0DC8-0DFC). As noted hereinabove, information contained in this code establishes the experimental conditions for the particular test such as wavelength for optical experiments or the electrode channel member for ion-selective electrode experiments. The information stored may also relate to incubation time, reagent and sample volume units, calibration information for a particular reagent lot, lot number, expiration date, clinical significant range and test title. For example, the bar code may contain a slope and interrupt valves for synthesizing a straight-line calibration curve to correct for the particular reagent barch being used. In this way, new tests may be provided by the test reagent manufacturer without requiring changes in the instrumentation or software associated with the analyzer of the present invention, but only in the bar code associated with the reagent package or container.

The system is also provided with certain primitive instructions so that new input/output devices or capabilities may be added without the need to change the system software. For example, these commands provide the expansion capability for new experiments. One such primitive command is "K" followed by an address and value which permits the value to be transmitted to any location in the experimental I/O space of the system (memory locations 0F55-0F64). The command "D" followed by a numerical value provides a time delay in tenths of a second via timer 68 (memory locations 0CEA-0CFF). The command "C" followed by a numerical value 0-7 permits any individual channel of analog multiplexer 73 to be selected (memory locations 0BF1-0C23). Finally, the command "A" obtains a reading from A/D converter 67 (memory locations 0C58-0C5C). These primitive commands may be combined with those noted hereinabove to produce more complex instructions for carrying out any particular test.

It will be observed that the results of the particular test may be displayed by any of the output devices described hereinabove. For example, all or part of the test may be displayed in the form of a histogram or bar graph on CRT display 57. In lieu of or in addition to such display, such results may be graphed by means of incremental plotter 58.

As noted above, a complete program listing for an exemplary program to control the processing described in connection with the chemical analyzer of the present invention, is listed in Appendix 1. It will be understood that this program may be stored on any suitable storage media, such as disc or tape, and read into RAM 55 when appropriate. Alternately, the program may be stored as "firmware" in system ROM 53 or control ROM 54.

It will be further understood that various changes in the details, steps, materials and arrangements of parts, which have been herein described and illustrated in order to explain the nature of the invention, may be made by those skilled in the art within the principle and scope of the invention as expressed in the appended claims.

APPENDIX I

|      | 00 | 01 | 02 | 03 | 04 | 05 | 06 | 07 | 08 | 09 | 0A | 0B | 0C | 0D | 0E | 0F |
|------|----|----|----|----|----|----|----|----|----|----|----|----|----|----|----|----|
| 0000 | 59 | 55 | 32 | 2E | 30 | 30 | 00 | 30 | 00 | EF | 00 | D4 | 01 | F6 | 01 | F4 |
| 0010 | 02 | 03 | 01 | D4 | 02 | 1E | 03 | A6 | 03 | B2 | 03 | C4 | 00 | 2C | 04 | 9E |
| 0020 | 04 | 8C | 03 | F1 | 03 | DE | 03 | EC | 04 | CA | 01 | 10 | 6E | 9F | 80 | 41 |
| 0030 | 30 | 8C | CD | 34 | 10 | FC | 04 | 38 | E3 | E4 | DD | 41 | 35 | 06 | 86 | 03 |
| 0040 | B7 | 30 | 0A | 86 | 35 | B7 | 30 | 0A | 17 | 04 | 6D | B6 | 40 | 60 | B7 | 87 |
| 0050 | 01 | 8A | 20 | B7 | 87 | 02 | B7 | 87 | 03 | 86 | 80 | B7 | 87 | 0B | 8E | 00 |
| 0060 | FD | BF | 87 | 04 | 30 | 8D | 04 | 76 | 10 | 8E | 00 | 28 | E6 | 80 | 8D | 78 |
| 0070 | 4C | 31 | 3F | 26 | F7 | CC | 40 | 00 | 8D | 6E | 8E | C2 | 00 | B7 | 28 | 00 |
| 0080 | 30 | 01 | 26 | F9 | CC | 49 | 00 | 8D | 5F | 8D | 37 | CC | 4D | 00 | 8D | 58 |
| 0090 | 8D | 30 | CC | 41 | 00 | 8D | 3D | CC | C1 | 10 | 8D | 38 | CC | 03 | 35 | B7 |
| 00A0 | 38 | 0A | F7 | 38 | 0A | 86 | 12 | B7 | 30 | 0F | 86 | 00 | B7 | 30 | 0E | 86 |
| 00B0 | 16 | B7 | 30 | 0F | 86 | 5E | B7 | 87 | 00 | 17 | 01 | 18 | B6 | 40 | 0B | 16 |
| 00C0 | 01 | 81 | 30 | 8D | 04 | 20 | 10 | 8E | 03 | 00 | A6 | 80 | B7 | 28 | 00 | 31 |
| 00D0 | 3F | 26 | F7 | 39 | 34 | 02 | 86 | 60 | 8D | 0E | 35 | 02 | 10 | 8E | 00 | 10 |
| 00E0 | B7 | 28 | 00 | 31 | 3F | 26 | F9 | 39 | F7 | 28 | 01 | B7 | 28 | 01 | 39 | 8D |
| 00F0 | 0D | 34 | 02 | AD | 9F | 87 | 04 | A1 | E4 | 26 | F8 | 35 | 02 | 39 | 36 | 02 |
| 0100 | 17 | 02 | C1 | B6 | 87 | 02 | 84 | 10 | 37 | 02 | 27 | 04 | AD | 9F | F8 | 0A |
| 0110 | 81 | 0A | 26 | 06 | 7C | 87 | 08 | 16 | 00 | F5 | 81 | 0D | 26 | 06 | 7F | 87 |
| 0120 | 07 | 16 | 00 | EB | 81 | 7F | 26 | 0D | 7D | 87 | 07 | 10 | 27 | 00 | E0 | 7A |
| 0130 | 87 | 07 | 16 | 00 | DA | 17 | 00 | D7 | 34 | 02 | 81 | 39 | 2E | 07 | 81 | 30 |
| 0140 | 2D | 03 | BA | 87 | 0B | B7 | 28 | 00 | 35 | 02 | 7C | 87 | 07 | 16 | 00 | BF |
| 0150 | 34 | 30 | 10 | 8E | 44 | 00 | 10 | BF | 87 | 0C | 10 | 8E | 04 | 20 | 10 | BF |

```
0160 87 0E 7F 87 0A B6 87 0E F6 87 0F 17 FF 7A 8E 00
0170 00 C6 20 B6 28 00 A7 89 87 92 30 01 5A 26 F4 B6
0180 87 0C F6 87 0D 17 FF 60 8E 00 00 C6 20 A6 89 87
0190 92 B7 28 00 30 01 5A 26 F4 10 BE 87 0C 31 A8 20
01A0 10 BF 87 0C 10 BE 87 0E 31 A8 20 10 BF 87 0E 7C
01B0 87 0A 86 17 B1 87 0A 26 AC C6 20 86 20 B7 28 00
01C0 5A 26 FA C6 17 F7 87 08 7F 87 07 CC 46 E0 17 FF
01D0 17 35 30 39 34 22 10 8E 03 00 CC 44 00 17 FF 08
01E0 86 20 B7 28 00 31 3F 26 F9 7F 87 07 7F 87 08 8D
01F0 1E 35 22 39 8D 0D A6 80 B1 87 00 27 05 17 FE FE
0200 20 F4 39 36 02 86 0D 17 FE F4 86 0A 16 FE EF 7F
0210 87 06 34 06 B6 87 07 F6 87 08 8D 02 35 86 81 1F
0220 2F 04 86 00 CB 01 C1 17 2F 03 16 FF 23 B7 87 07
0230 F7 87 08 86 20 3D C3 04 00 F3 87 06 84 3F 8A 40
0240 16 FE A5 CC 40 00 17 FE 9F 30 8D 00 7B 10 8E 00
0250 C0 A6 80 B7 28 00 31 3F 26 F7 CC 47 00 17 FE 88
0260 30 8D 01 24 C6 10 A6 80 B7 28 00 5A 26 F8 30 8D
0270 01 26 10 8E 87 11 C6 09 A6 80 A7 A0 5A 26 F9 39
0280 36 36 F1 87 11 2E 2F 8D 30 E6 80 58 58 10 AE 81
0290 A6 80 36 06 86 47 17 FE 4F 37 06 C0 04 1E 02 8D
02A0 20 1E 89 8D 1C 1E 89 1E 02 36 06 A6 80 48 48 8D
02B0 10 37 06 4A 26 DC 37 36 39 58 58 58 8E 87 12 3A
02C0 39 B7 28 00 12 12 39 39 00 00 00 00 00 00 00 00
02D0 00 00 00 00 00 00 00 00 00 00 00 00 00 00 00 00
02E0 00 00 00 00 00 00 00 00 F0 98 CE 40 70 16 3C 18
02F0 00 00 00 00 00 00 00 00 0F 19 73 02 0E 68 3C 18

00 01 02 03 04 05 06 07 08 09 0A 0B 0C 0D 0E 0F
0300 00 00 00 00 00 00 00 00 00 60 30 3E 0E 18 00 00
0310 00 00 00 00 00 00 00 00 00 06 0C 7C 70 18 00 00
0320 00 00 00 00 00 00 00 00 F2 99 8F 81 C1 47 6D 39
0330 00 00 00 00 00 00 00 00 4F 99 F1 81 83 E2 B6 9C
0340 00 00 00 00 00 00 00 00 F2 F9 FF FF FF 7F 7D 39
0350 00 00 00 00 00 00 00 00 4F 9F FF FF FF FF BE 9C
0360 00 00 00 00 00 00 00 00 FF FF FF FF F0 F0 F0 F0
0370 F0 F0 F0 F0 FF FF FF FF FF FF FF FF 0F 0F 0F 0F
0380 0F 0F 0F 0F FF FF FF FF D0 70 04 04 38 70 08 0C
0390 38 70 0C 06 38 70 10 0A 01 03 10 30 04 04 03 02
03A0 01 8D 03 27 FC 39 8D 0A 27 07 B6 38 0B 84 7F 1C
03B0 FB 39 34 02 B6 87 01 84 40 88 40 27 05 B6 38 0A
03C0 84 01 35 82 36 04 F6 87 02 C4 40 26 0A F6 38 0A
03D0 C5 02 27 F9 B7 38 0B 37 04 39 7C 87 07 39 17 00
03E0 AB 26 08 8D CD 26 04 AD 9F F8 08 39 8D 03 16 00
03F0 7F 36 06 B6 87 02 84 08 26 23 7C 87 10 B6 87 10
0400 81 FF 26 19 7F 87 10 7A 87 13 FC 40 12 86 06 57
0410 4A 26 FC FB 87 14 F7 87 14 5F 17 FE 63 37 06 8D
0420 91 27 02 20 85 8D 65 27 03 16 00 78 AD 9F F8 08
0430 27 BF 6E 9F F8 04 8D A2 36 14 C6 50 9E 3D 8D B1
0440 81 1B 27 21 81 0D 26 04 A7 82 20 1B 81 7F 26 09
0450 9C 3D 27 EA 30 1F 5C 20 09 5D 27 E2 A7 80 81 3A
0460 27 05 5A 20 D9 30 1F 9F 3F 86 5E A7 01 37 14 39
0470 34 04 F6 87 02 34 04 F6 87 03 F7 87 02 17 FC 7E
0480 35 04 F7 87 02 35 84 8D 03 27 FC 39 34 02 B6 87
0490 01 84 20 88 20 27 05 B6 30 0F 84 80 35 82 8D E7
04A0 8D EA 27 13 B6 30 0E 81 5A 26 04 86 7F 20 06 81
04B0 5B 26 02 86 2D 1C FB 39 7F 30 0D 86 FF B7 30 0C
04C0 86 3E B7 30 0D 39 7D 30 0D 39 8D FA 2A FC 7D 30
```

```
       00 01 02 03 04 05 06 07 08 09 0A 0B 0C 0D 0E 0F
04D0   0C B7 30 0C 86 36 8D F6 86 3E B7 30 0D 39 00 C2
04E0   01 80 01 0E 00 01 00 00 00 00 00 00 00 00 20 20
04F0   20 20 20 00 20 00 50 50 50 00 00 00 00 00 50 50
0500   F8 50 F8 50 50 00 20 78 A0 70 28 F0 20 00 C0 C8
0510   10 20 40 98 18 00 40 A0 A0 40 A8 90 68 00 20 20
0520   20 00 00 00 00 00 20 40 80 80 80 40 20 00 20 10
0530   08 08 08 10 20 00 20 A8 70 20 70 A8 20 00 00 20
0540   20 F8 20 20 00 00 00 00 00 00 20 20 40 00 00 00
0550   00 F8 00 00 00 00 00 00 00 00 00 00 20 00 00 08
0560   10 20 40 80 00 00 70 88 98 A8 C8 88 70 00 20 60
0570   20 20 20 20 70 00 70 88 08 30 40 80 F8 00 F8 08
0580   10 30 08 88 70 00 10 30 50 90 F8 10 10 00 F8 80
0590   F0 08 08 88 70 00 38 40 80 F0 88 88 70 00 F8 08
05A0   10 20 40 40 40 00 70 88 88 70 88 88 70 00 70 88
05B0   88 78 08 10 E0 00 00 00 20 00 20 00 00 00 00 00
05C0   20 00 20 20 40 00 10 20 40 80 40 20 10 00 00 00
05D0   F8 00 F8 00 00 00 40 20 10 08 10 20 40 00 70 88
05E0   10 20 20 00 20 00 70 88 A8 B8 B0 80 78 00 20 50
05F0   88 88 F8 88 88 00 F0 88 99 F0 88 88 F0 00 70 88

00 01 02 03 04 05 06 07 08 09 0A 0B 0C 0D 0E 0F
0600   80 80 80 88 70 00 F0 88 88 88 88 88 F0 00 F8 80
0610   80 F0 80 80 F8 00 F8 80 80 F0 80 80 80 00 78 80
0620   80 80 98 88 78 00 88 88 88 F8 88 88 88 00 70 20
0630   20 20 20 20 70 00 08 08 08 08 08 88 70 00 88 90
0640   A0 C0 A0 90 88 00 80 80 80 80 80 80 F8 00 88 D8
0650   A8 A8 88 88 88 00 88 88 C8 A8 98 98 88 00 70 88
0660   88 88 88 88 70 00 F0 88 88 F0 80 80 80 00 70 88
0670   88 88 A8 90 68 00 F0 88 88 F0 A0 90 88 00 70 88
0680   80 70 08 88 70 00 F8 20 20 20 20 20 20 00 88 88
0690   88 88 88 88 70 00 88 88 88 88 88 50 20 00 88 88
06A0   88 A8 A8 D8 88 00 88 88 50 20 50 88 88 00 88 88
06B0   50 20 20 20 20 00 F8 08 10 20 40 80 F8 00 F8 C0
06C0   C0 C0 C0 C0 F8 00 00 80 40 20 10 08 00 00 F8 18
06D0   18 18 18 18 F8 00 20 70 A8 20 20 00 00 00 00 20
06E0   40 F8 40 20 00 00 40 20 10 00 00 00 00 00 00 00
06F0   70 88 F8 88 88 00 00 00 F0 48 70 48 F0 00 00 00
0700   78 80 80 80 78 00 00 00 F0 48 48 48 F0 00 00 00
0710   F0 80 E0 80 F0 00 00 00 F0 80 E0 80 80 00 00 00
0720   78 80 B8 88 70 00 00 00 88 88 F8 88 88 00 00 00
0730   F8 20 20 20 F8 00 00 00 70 20 20 A0 E0 00 00 00
0740   90 A0 A0 C0 90 00 00 00 80 80 80 80 F8 00 00 00
0750   88 D8 A8 88 88 00 00 00 88 C8 A8 98 88 00 00 00
0760   F8 88 88 88 F8 00 00 00 F0 88 F0 80 80 00 00 00
0770   F8 88 A8 90 E0 00 00 00 F8 88 F8 A0 90 00 00 00
0780   78 80 70 08 F0 00 00 00 F8 20 20 20 20 00 00 00
0790   88 88 88 88 70 00 00 00 88 88 90 A0 40 00 00 00
07A0   88 88 A8 D8 88 00 00 00 88 60 20 60 88 00 00 00
07B0   88 50 20 20 20 00 00 00 F8 10 20 40 F8 00 38 40
07C0   20 C0 20 40 38 00 40 20 10 08 10 20 40 00 E0 10
07D0   20 18 20 10 E0 00 40 A8 10 00 00 00 00 00 FF FF
07E0   FF FF FF FF FF FF FF FF FF FF FF FF FF FF FF FF
07F0   FF FF FF FF FF FF FF FF FF FF FF FF FF FF FF FF 00 01 02 03 04 05 06 07 08 09 0A 0B 0C 0D 0E 0F
0800   41 4E 47 2E 30 30 86 80 1E 8B CE 82 FF CC 81 80
0810   DD 3D CC 81 D0 DD A9 B6 87 03 84 BF B7 87 03 86
0820   00 B7 40 05 B7 40 07 B7 40 04 86 FE B7 40 06 86
```

```
0830 06 B7 40 05 86 14 B7 40 07 17 04 81 86 82 B7 40
0840 11 86 A0 B7 40 10 86 83 B7 40 11 86 82 B7 40 10
0850 CC 00 00 DD 94 CC FF FF DD 9A 86 00 97 A4 97 8C
0860 86 7F 97 A2 97 A3 5F 17 05 2A 86 7F C6 01 17 05
0870 23 86 20 B7 40 05 86 00 B7 40 04 86 22 B7 40 05
0880 17 02 F4 B6 40 0B 30 8D 00 35 86 00 8D 17 5D 26
0890 08 8B 08 81 20 26 F5 20 3F 30 8D 00 1A AD 9F F8
08A0 10 6E 9F F8 02 34 02 5F 1F 02 C6 04 A6 80 A1 A0
08B0 26 03 5A 26 F7 35 82 45 58 50 45 43 54 45 44 59
08C0 55 32 2E 30 30 41 4E 47 2E 30 30 50 4C 34 2E 30
08D0 30 49 4E 30 2E 30 30 5E AD 9F 18 06 0F C6 CC FF
08E0 03 AD 9F 10 1C 17 06 98 17 02 CB 10 83 0D AC 2B
08F0 F7 17 03 69 17 04 1C 17 02 4D 17 02 9A 86 0D 8D
0900 2F 8D 31 17 00 97 20 F9 6E 9F F8 2E 6E 9F 10 1A
0910 6E 9F F8 02 6E 9F 00 14 6E 9F 00 16 6E 9F 00 18
0920 6E 9F 00 1A 6E 9F 00 1C 6E 9F 00 1E 6E 9F 00 20
0930 6E 9F 00 06 10 8E 81 80 8D E6 10 9E 3D A6 A0 81
0940 3A 27 2D 10 9C 3F 27 2F 81 20 27 F1 81 3B 27 ED
0950 81 40 2D 1D 30 8D 00 52 AD 9F F8 26 26 1F 9F C7
0960 30 8D FE 9C 1F 10 E3 9F 80 C7 1F 01 AD 84 20 CD
0970 39 8D 08 86 01 20 08 86 02 20 04 20 B3 86 03 34
0980 02 8D 1E 86 5B 8D F4 35 02 8B 30 8D EE 86 5D 8D
0990 EA 8D 0E 10 CE 86 FF CE 82 FF 16 FF 64 86 23 8D
09A0 DA 86 0D 8D D6 86 0A 8D D2 39 41 04 58 42 01 F9
09B0 43 03 F1 44 04 EA 45 04 23 46 02 7A 47 03 47 48
09C0 03 31 49 04 24 4A 03 36 4B 07 55 4C 05 76 4D 01
09D0 F9 4E 05 13 4F 03 C2 50 04 3A 51 04 C7 52 05 C8
09E0 53 03 97 54 03 B1 57 02 3D 58 03 77 59 07 52 5A
09F0 04 5D 5B 07 64 40 01 10 00 39 AD 9F 10 16 29 01
0A00 39 86 05 16 FF 79 DD 98 96 8B 84 FB 8A 00 8A B0
0A10 8D 5A DC 98 93 94 DD 96 2A 0E 4F 5F 93 96 DD 96
0A20 96 8B 84 FB 8A 04 97 8B DC 96 FD 40 16 DC 9A FD
0A30 40 12 96 8B 84 47 8D 34 DC 98 DD 94 39 8D 23 34
0A40 06 CC 20 00 97 9A 35 06 8D BC 86 64 97 87 B6 40
0A50 11 84 04 26 0C 17 01 2C 0A 87 2A F2 86 04 16 FF
0A60 1E 39 17 FF 95 83 01 2C C3 01 20 39 34 04 C6 14
0A70 F7 40 07 B7 40 06 97 8B 35 84 0F C5 8D E4 DD 9C
0A80 CC 06 02 84 07 9A A4 97 9E 8D 69 DC 94 83 01 20
0A90 58 49 34 30 1F 01 30 89 88 00 8D 6E 0D C5 26 02
0AA0 A3 84 0D C6 26 05 17 FE 63 20 21 34 36 1F 02 9E
0AB0 94 0D C6 2B 10 34 30 CC FF 02 AD 9F 10 1C CC 00
0AC0 03 8D 11 35 30 CC 02 03 8D 0A 35 36 0D A0 26 CA
0AD0 0F C6 35 B0 34 36 1F 10 83 01 2C 58 49 58 49 58
0AE0 49 58 49 83 10 00 1F 01 35 06 0F C6 0A C6 AD 9F
0AF0 10 1C 35 B0 CC FF FF DD 9A 17 02 68 17 00 D2 DC 00 01 02 03 04 05 06 07 08 09 0A 0B 0C 0D 0E 0F
0B00 9E 17 02 90 17 02 0B 16 FD FE 34 10 17 FD F9 35
0B10 10 34 06 0F A0 DC 94 10 93 9C 27 13 2B 07 83 00
0B20 01 30 1E 20 05 C3 00 01 30 02 17 FF 12 0C A0 35
0B30 86 CC 07 02 20 03 CC 00 02 DD 9E 0F C5 0C C5 17
0B40 FF 20 DD 9C 16 FF 42 CC 01 2C 17 FF 19 17 FE EF
0B50 CC 06 02 84 07 9A A4 DD 9E CC 03 20 17 FF 06 DD
0B60 9C 8E 88 00 8D 8E 8D A2 ED 84 0D A0 26 F8 CC 01
0B70 F4 17 FE F1 16 FE C8 8E 88 00 4F 5F ED 81 8C 8F
0B80 FE 26 F9 39 34 06 C6 63 21 FE 86 63 12 21 F9 4A
0B90 2A FA 5A 2A F3 35 86 30 8D 00 04 6E 9F 00 0C 41
0BA0 6E 61 6C 79 7A 65 72 20 52 45 56 20 47 2E 30 30
```

```
0BB0  5E 8D 03 16 FD 56 4F 17 00 18 CC 01 02 17 01 D4
0BC0  20 72 17 01 9F 17 FE 75 17 01 35 17 01 1C 16 00
0BD0  87 4F 34 02 46 84 02 9A 8B 17 FE 90 96 A1 84 9F
0BE0  97 A1 35 02 46 46 46 46 84 60 9A A1 97 A1 16 01
0BF0  77 17 FE 06 DD C9 1F 98 17 FF D7 17 FD FC 4F C4
0C00  07 DD C7 17 FD F4 1F 98 84 07 97 C7 34 10 9E C9
0C10  A6 89 80 8C 84 07 9A C7 A7 89 80 8C D6 C8 35 10
0C20  16 01 71 39 86 01 17 FF A9 CC 01 02 17 01 65 8D
0C30  03 16 FC D8 17 FC D1 16 FC CE 17 00 C3 17 FD BA
0C40  DD A7 4F 5F DD 84 0C 85 26 02 0C 84 17 FC B9 93
0C50  A7 2A F3 DC 84 16 FC B4 8D DA 16 FC AF CC 1B 58
0C60  DD 94 17 00 FF 17 FF 69 CC 07 02 8A C8 17 01 24
0C70  8D 4B B6 40 06 CC 20 00 DD 9A 17 FC 8B 10 83 04
0C80  00 2E F7 CC 00 00 17 FD 7D B6 40 06 84 01 27 09
0C90  B6 40 07 84 40 26 1F 27 F0 8D 22 96 8C 84 07 94
0CA0  A4 97 8C C6 02 17 00 EC CC 00 00 DD 94 CC 01 2C
0CB0  17 FD B2 16 FD 89 8D 05 86 09 16 FC C2 86 F8 17
0CC0  FD AA 86 F0 16 FD A5 17 02 B6 4D 26 17 17 FE E6
0CD0  83 0E 74 17 02 9E 10 83 00 14 2E 08 30 8D 00 07
0CE0  6E 9F 00 0C 16 03 01 4F 4B 5E 17 FD 0D 34 20 1F
0CF0  02 10 8C 00 01 2D 07 17 FE 8A A6 A2 20 F3 35 A0
0D00  8D 62 17 FD 38 17 FE C9 CC 06 02 84 07 9A A4 17
0D10  00 82 39 8D 5B 4F 17 FE B9 CC 00 14 8D CF CC 07
0D20  02 8D 71 96 A2 5F 8D 6C 17 FB DD 4D 2C 04 0C A2
0D30  20 EC 10 83 00 16 2F 04 0A A2 20 E2 CC 00 02 8D
0D40  53 96 A3 C6 01 8D 4D 17 FB BE 4D 2C 04 0C A3 20
0D50  EB 10 83 00 16 2F 04 0A A3 20 E6 8D 07 CC 00 14
0D60  17 FF 8A 39 96 A1 84 EF 97 A1 8A 8F B7 40 A0 39
0D70  96 A1 8A 10 20 F2 17 FC 81 C1 00 27 F3 20 E5 C4
0D80  0F D7 C3 D6 A1 CA 80 C4 F0 DA C3 F7 40 A0 D7 A1
0D90  B6 40 40 39 C4 0F D7 C3 D6 A1 C4 70 DA C3 D7 A1
0DA0  B7 40 80 F7 40 A0 39 2A 2A 2A 5E 7C 20 20 5E 2E
0DB0  2E 2E 5E 3C 3C 3C 5E 3E 3E 3E 5E 30 8C E9 4A 1E
0DC0  89 58 58 3A 6E 9F 00 0C 8D 35 C1 2B 27 04 86 02
0DD0  20 E9 4D 26 E6 34 10 9E A9 E6 80 C1 2B 27 06 86
0DE0  01 8D D8 20 18 E6 80 36 10 30 8D 01 38 3A A6 84
0DF0  81 2A 27 03 17 FB 39 37 10 9C AB 2D E8 35 90 36

00 01 02 03 04 05 06 07 08 09 0A 0B 0C 0D 0E 0F
0E00  30 B6 40 60 47 25 FA 9E A9 4F 36 12 8D 22 37 12
0E10  C1 2C 27 18 E7 80 C1 2B 26 03 4D 26 09 4C 81 1E
0E20  2F E8 86 03 20 03 9F AB 4F 37 30 39 86 01 20 F9
0E30  0F C2 86 09 97 AD 4F 5F DD AE 8E 80 B0 B6 40 60
0E40  47 24 FA 10 8E 00 00 B6 40 60 31 21 84 01 98 C2
0E50  26 F5 1F 20 ED 81 D3 AE DD AE 96 C2 88 01 84 01
0E60  97 C2 0A AD 26 DD DC AE 0F AF 0F AE 10 8E 00 08
0E70  44 56 44 56 1F 01 D3 AE DD AE 1F 10 31 3F 26 F0
0E80  DC AE 44 56 C3 00 01 44 56 DD AE 44 56 D3 AE DD
0E90  AE 10 8E 80 B0 8E 00 00 1F 10 58 49 1F 01 EC A1
0EA0  10 93 AE 2D 02 30 01 10 8C 80 C2 2D EB 1F 10 10
0EB0  8E 00 00 30 8D 00 14 10 A3 81 27 0C 31 21 10 8C
0EC0  00 2B 2F F3 10 8E 00 2C 1F 20 39 00 34 01 21 00
0ED0  61 01 60 00 31 01 30 00 70 00 25 01 24 00 64 01
0EE0  09 00 49 01 48 00 19 01 18 00 58 00 0D 01 0C 00
0EF0  4C 00 1C 01 03 00 43 01 42 00 13 01 12 00 52 00
0F00  07 01 06 00 46 00 16 01 81 00 C1 01 C0 00 91 01
0F10  90 00 D0 00 85 01 84 00 C4 00 A8 00 A2 00 8A 00
```

```
0F20 2A 00 94 0F FF 30 31 32 33 34 35 36 37 38 39 41
0F30 42 43 44 45 46 47 48 49 4A 4B 4C 4D 4E 4F 50 51
0F40 52 53 54 55 56 57 58 59 5A 2D 2C 20 24 2F 2B 25
0F50 2A 3F 0C C6 39 17 FA A2 D7 CE 17 FA 9D 1E 89 D6
0F60 CE 16 FE 30 17 FA 93 96 A3 34 04 17 FE 26 35 04
0F70 0C A3 20 F3 10 83 00 00 2A 05 43 53 C3 00 01 39
0F80 30 8D 00 2A A6 81 2B 23 17 FC 47 EC 81 C1 7F 27
0F90 03 17 FE 00 17 FC 9D A3 81 8D D9 10 A3 80 2F E4
0FA0 30 8D 00 44 AD 9F 00 0C 86 FF 39 86 00 39 00 00
0FB0 03 02 F6 50 00 14 00 00 04 02 09 C4 00 14 00 00
0FC0 05 02 F7 CC 00 C8 00 04 00 7F 09 C4 00 64 00 05
0FD0 00 7F F6 3C 00 64 00 06 00 7F 09 C4 00 64 00 07
0FE0 00 7F 00 00 00 04 FF FF 18 53 59 53 54 45 4D 20
0FF0 45 52 52 4F 52 5E FF FF FF FF FF FF FF FF FF FF 00 01 02 03 04 05 06 07 08 09 0A 0B 0C 0D 0E 0F
1000 50 4C 34 2E 30 30 10 BA 11 0E 10 66 10 35 10 1E
1010 11 42 11 42 11 43 11 6A 11 B3 11 CD 13 20 8D 15
1020 29 12 1E 02 10 83 00 00 2A 02 8D 03 1E 02 39 43
1030 53 C3 00 01 39 33 5E 6F C4 6F 41 4D 2A 06 6A C4
1040 6A 41 8D EB 1E 02 4D 2A 04 6C C4 8D E2 1E 02 8D
1050 15 29 E1 6D C4 27 06 1E 02 8D D4 1E 02 6D 41 27
1060 02 8D CC 33 42 39 34 16 8E FF FF 36 10 1F 31 36
1070 20 1F 32 4F 36 02 4C 81 11 27 33 A7 C4 68 21 69
1080 A4 24 F3 6A C4 66 A4 66 21 66 A4 66 21 35 06 10
1090 A3 A4 2D 02 A3 A4 69 01 69 84 64 A4 66 21 6A C4
10A0 26 ED 63 84 63 01 33 43 37 20 6F 84 35 90 86 0F
10B0 1F 8A 33 41 37 20 33 42 35 96 34 10 36 06 1F 31
10C0 36 20 1F 32 A6 21 E6 01 3D 36 06 A6 A4 E6 01 3D
10D0 36 06 A6 21 E6 84 3D 36 06 A6 A4 E6 84 3D 36 06
10E0 EC 42 E3 44 ED 44 24 02 6C C4 E6 46 4F E3 44 24
10F0 02 6C C4 ED 45 1F 89 4F E3 C4 1F 02 26 0C 86 0F
1100 1F 8A 34 01 EC 46 33 48 35 91 86 00 20 F2 33 5F
1110 6F C4 4D 2A 05 6A C4 17 FF 15 1E 02 4D 2A 05 6C
1120 C4 17 FF 0B 8D 94 10 29 FF 0A 6D C4 17 FF 00 1E
1130 02 25 02 6F C4 43 53 6D C4 27 03 C3 00 01 33 41
1140 39 39 39 E6 A0 C1 20 27 FA C1 3B 27 18 C1 2C 27
1150 14 C1 3A 27 10 C0 30 2B 07 C1 09 2E 03 1C FC 39
1160 1C FC 1A 02 39 1C FC 1A 01 39 34 02 6F E4 CC 00
1170 00 DD 43 36 10 8D CC 25 21 29 32 4F 36 06 DC 43
1180 D3 43 1F 01 DD 43 D3 43 DD 43 D3 43 9F 43 D3 43
1190 DD 43 37 06 D3 43 DD 43 20 DB 6D E4 27 06 4F 5F
11A0 93 43 DD 43 35 02 DC 43 37 10 1C FC 39 37 10 35
11B0 02 20 AD 34 02 6F E4 A6 A0 81 20 27 FA 81 2B 27
11C0 AD 81 2D 27 04 A6 A2 20 A5 6A E4 20 A1 36 30 36
11D0 06 86 2B E6 C4 2A 08 4F 5F A3 C4 ED C4 86 2D 8D
11E0 31 37 06 10 8E 03 E8 8D 19 10 8E 00 64 8D 13 10
11F0 8E 00 0A 8D 0D CB 30 1F 98 8D 17 86 3B 8D 13 37
1200 30 39 17 FE 61 36 06 1F 20 1F 98 8A 30 8D 03 37
1210 06 39 6E 9F 00 06 34 06 34 30 30 8D 00 EE 81 0A
1220 26 05 E6 02 4F 20 59 A1 80 2E 04 A0 80 2C 05 A6
1230 03 5F 20 F1 30 04 36 02 6A C4 2B 05 E6 80 3A 20
1240 F7 37 02 A6 80 36 06 4F 36 02 6C C4 A6 80 81 FF
1250 26 08 6F C4 6C C4 6A 41 20 F2 E6 80 6A 41 A6 80
1260 34 10 AE 62 10 AE 64 8D 25 35 10 A6 C4 2B 05 27
1270 04 43 20 01 4F A7 C4 6A 41 26 DF 37 02 37 06 4F
1280 35 30 36 02 6F C4 6C C4 8D 04 37 02 35 86 34 06
```

```
1290 1D 34 20 E3 E4 1F 02 35 06 35 06 1F 89 1D 34 10
12A0 E3 E4 1F 01 35 06 8D 05 A6 C4 16 01 12 34 06 84
12B0 80 36 02 86 9B 3D 44 56 44 56 44 56 44 56 36 06
12C0 17 FE 4B 37 06 36 20 1E 12 17 FE 42 36 20 1E 12
12D0 4F 20 12 1F 89 AF C4 10 AF 42 67 21 66 C4 67 43
12E0 66 42 5A 26 F5 66 45 34 01 1E 01 25 04 A3 42 20
12F0 02 E3 42 1E 01 35 01 1E 02 25 04 E3 C4 20 02 A3

00 01 02 03 04 05 06 07 08 09 0A 0B 0C 0D 0E 0F
1300 C4 1E 02 4C 81 08 26 CB 33 45 35 86 65 30 20 1C
1310 0E 14 00 F4 F8 F7 FF 00 F4 08 09 FF FB 02 05 02
1320 4D 2A 10 57 24 03 17 01 61 57 25 01 39 86 0C 6E
1330 9F F8 0A 81 03 2C 0C 57 24 03 17 00 4B 57 10 25
1340 00 0C 39 39 C3 10 00 47 56 31 3F 26 FA 39 34 36
1350 1F 20 10 8E 00 05 8D EC 36 04 1F 10 10 8E 00 04
1360 8D E2 36 06 C6 1C A6 E4 81 03 26 02 C6 1D 36 04
1370 CC 0F 06 36 06 10 8E 00 06 8D 02 35 B6 37 02 AD
1380 9F F8 0A 31 3F 26 F6 39 34 36 1F 10 10 8E 00 02
1390 17 FF B1 1F 01 EC 64 10 8E 00 03 17 FF A6 1F 02
13A0 EC E4 8D 02 35 B6 34 36 C6 01 81 01 2E 0B 86 01
13B0 8D 0D 35 36 34 36 4D 27 04 86 FF 8D 02 35 B6 4D
13C0 27 0B 2B 04 86 09 20 02 86 0A 17 00 94 1F 10 93
13D0 45 97 4D 2A 03 17 FC 57 DD 49 9F 45 1F 20 93 47
13E0 97 4E 2A 03 17 FC 48 DD 4B 10 9F 47 10 93 49 2F
13F0 04 C6 04 20 01 5F 0D 4E 2A 02 CA 02 0D 4D 2A 02
1400 CA 01 30 8D 00 4B 58 3A A6 80 E6 84 34 06 DC 49
1410 10 93 4B 2C 08 1F 01 DC 4B 9F 4B DD 49 4F 5F DD
1420 4D 10 9E 49 31 21 31 3F 27 24 DC 4D D3 4B D3 4B
1430 DD 4D 10 93 49 2E 06 35 06 34 06 20 0C 93 49 93
1440 49 DD 4D 35 06 34 06 1E 89 17 00 15 20 D8 35 06
1450 39 72 71 76 77 72 73 76 75 70 71 70 77 74 73 74
1460 75 34 36 84 0F 1E 89 30 8D 00 10 3A A6 84 F6 40
1470 05 2A FB B7 40 04 F6 40 04 35 B6 10 11 01 03 02
1480 06 04 14 00 20 08 6E 9F F8 0A 34 36 4F B7 40 05
1490 86 FF B7 40 04 86 2E B7 40 05 4F 5F DD 45 DD 47
14A0 20 D1 58 2C 59 2C 3C 50 45 4E 20 5E 86 80 1E 8B
14B0 8D D8 30 8C ED AD 9F 00 0C 10 8E 81 80 10 9F 3D
14C0 AD 9F 00 1A 10 9E 3D 17 FC E9 36 06 17 FC E4 36
14D0 06 17 FC DF 1E 98 37 20 37 10 17 FE E2 20 D3 FF
14E0 FF FF FF FF FF FF FF FF FF FF FF FF FF FF FF FF
14F0 FF FF FF FF FF FF FF FF FF FF FF FF FF FF FF FF
1500 FF FF FF FF FF FF FF FF FF FF FF FF FF FF FF FF
1510 FF FF FF FF FF FF FF FF FF FF FF FF FF FF FF FF
1520 FF FF FF FF FF FF FF FF FF FF FF FF FF FF FF FF
1530 FF FF FF FF FF FF FF FF FF FF FF FF FF FF FF FF
1540 FF FF FF FF FF FF FF FF FF FF FF FF FF FF FF FF
1550 FF FF FF FF FF FF FF FF FF FF FF FF FF FF FF FF
1560 FF FF FF FF FF FF FF FF FF FF FF FF FF FF FF FF
1570 FF FF FF FF FF FF FF FF FF FF FF FF FF FF FF FF
1580 FF FF FF FF FF FF FF FF FF FF FF FF FF FF FF FF
1590 FF FF FF FF FF FF FF FF FF FF FF FF FF FF FF FF
15A0 FF FF FF FF FF FF FF FF FF FF FF FF FF FF FF FF
15B0 FF FF FF FF FF FF FF FF FF FF FF FF FF FF FF FF
15C0 FF FF FF FF FF FF FF FF FF FF FF FF FF FF FF FF
15D0 FF FF FF FF FF FF FF FF FF FF FF FF FF FF FF FF
15E0 FF FF FF FF FF FF FF FF FF FF FF FF FF FF FF FF
15F0 FF FF FF FF FF FF FF FF FF FF FF FF FF FF FF FF
```

|      | 00 | 01 | 02 | 03 | 04 | 05 | 06 | 07 | 08 | 09 | 0A | 0B | 0C | 0D | 0E | 0F |
|------|----|----|----|----|----|----|----|----|----|----|----|----|----|----|----|----|
| 1600 | FF | FF | FF | FF | FF | FF | FF | FF | FF | FF | FF | FF | FF | FF | FF | FF |
| 1610 | FF | FF | FF | FF | FF | FF | FF | FF | FF | FF | FF | FF | FF | FF | FF | FF |
| 1620 | FF | FF | FF | FF | FF | FF | FF | FF | FF | FF | FF | FF | FF | FF | FF | FF |
| 1630 | FF | FF | FF | FF | FF | FF | FF | FF | FF | FF | FF | FF | FF | FF | FF | FF |
| 1640 | FF | FF | FF | FF | FF | FF | FF | FF | FF | FF | FF | FF | FF | FF | FF | FF |
| 1650 | FF | FF | FF | FF | FF | FF | FF | FF | FF | FF | FF | FF | FF | FF | FF | FF |
| 1660 | FF | FF | FF | FF | FF | FF | FF | FF | FF | FF | FF | FF | FF | FF | FF | FF |
| 1670 | FF | FF | FF | FF | FF | FF | FF | FF | FF | FF | FF | FF | FF | FF | FF | FF |
| 1680 | FF | FF | FF | FF | FF | FF | FF | FF | FF | FF | FF | FF | FF | FF | FF | FF |
| 1690 | FF | FF | FF | FF | FF | FF | FF | FF | FF | FF | FF | FF | FF | FF | FF | FF |
| 16A0 | FF | FF | FF | FF | FF | FF | FF | FF | FF | FF | FF | FF | FF | FF | FF | FF |
| 16B0 | FF | FF | FF | FF | FF | FF | FF | FF | FF | FF | FF | FF | FF | FF | FF | FF |
| 16C0 | FF | FF | FF | FF | FF | FF | FF | FF | FF | FF | FF | FF | FF | FF | FF | FF |
| 16D0 | FF | FF | FF | FF | FF | FF | FF | FF | FF | FF | FF | FF | FF | FF | FF | FF |
| 16E0 | FF | FF | FF | FF | FF | FF | FF | FF | FF | FF | FF | FF | FF | FF | FF | FF |
| 16F0 | FF | FF | FF | FF | FF | FF | FF | FF | FF | FF | FF | FF | FF | FF | FF | FF |
| 1700 | FF | FF | FF | FF | FF | FF | FF | FF | FF | FF | FF | FF | FF | FF | FF | FF |
| 1710 | FF | FF | FF | FF | FF | FF | FF | FF | FF | FF | FF | FF | FF | FF | FF | FF |
| 1720 | FF | FF | FF | FF | FF | FF | FF | FF | FF | FF | FF | FF | FF | FF | FF | FF |
| 1730 | FF | FF | FF | FF | FF | FF | FF | FF | FF | FF | FF | FF | FF | FF | FF | FF |
| 1740 | FF | FF | FF | FF | FF | FF | FF | FF | FF | FF | FF | FF | FF | FF | FF | FF |
| 1750 | FF | FF | FF | FF | FF | FF | FF | FF | FF | FF | FF | FF | FF | FF | FF | FF |
| 1760 | FF | FF | FF | FF | FF | FF | FF | FF | FF | FF | FF | FF | FF | FF | FF | FF |
| 1770 | FF | FF | FF | FF | FF | FF | FF | FF | FF | FF | FF | FF | FF | FF | FF | FF |
| 1780 | FF | FF | FF | FF | FF | FF | FF | FF | FF | FF | FF | FF | FF | FF | FF | FF |
| 1790 | FF | FF | FF | FF | FF | FF | FF | FF | FF | FF | FF | FF | FF | FF | FF | FF |
| 17A0 | FF | FF | FF | FF | FF | FF | FF | FF | FF | FF | FF | FF | FF | FF | FF | FF |
| 17B0 | FF | FF | FF | FF | FF | FF | FF | FF | FF | FF | FF | FF | FF | FF | FF | FF |
| 17C0 | FF | FF | FF | FF | FF | FF | FF | FF | FF | FF | FF | FF | FF | FF | FF | FF |
| 17D0 | FF | FF | FF | FF | FF | FF | FF | FF | FF | FF | FF | FF | FF | FF | FF | FF |
| 17E0 | FF | FF | FF | FF | FF | FF | FF | FF | FF | FF | FF | FF | FF | FF | FF | FF |
| 17F0 | FF | FF | FF | FF | FF | FF | FF | FF | FF | FF | FF | FF | FF | FF | FF | FF |

|      | 00 | 01 | 02 | 03 | 04 | 05 | 06 | 07 | 08 | 09 | 0A | 0B | 0C | 0D | 0E | 0F |
|------|----|----|----|----|----|----|----|----|----|----|----|----|----|----|----|----|
| 1800 | 49 | 4E | 30 | 2E | 30 | 30 | 18 | 0C | 18 | 3A | 19 | EF | B6 | 87 | 01 | 34 |
| 1810 | 02 | 84 | 20 | 88 | 20 | 97 | 4A | 35 | 02 | 84 | 04 | 88 | 04 | 97 | 49 | 86 |
| 1820 | B5 | B7 | 40 | 0A | 30 | 8C | D9 | CC | 18 | F6 | 34 | 10 | E3 | E4 | DD | 42 |
| 1830 | 35 | 06 | CC | 18 | 3A | DD | F4 | 1C | EF | 39 | B6 | 40 | 0A | 2A | 03 | 16 |
| 1840 | 01 | 01 | B6 | 38 | 0B | 2A | 03 | 16 | 00 | 53 | B6 | 30 | 0B | 2A | 03 | 16 |
| 1850 | 00 | 75 | B6 | 30 | 0D | 2A | 03 | 16 | 00 | 10 | B6 | 30 | 0E | 2A | 03 | 16 |
| 1860 | 00 | 2B | 96 | 4D | 2A | 03 | 16 | 00 | 78 | 3B | 96 | 45 | 26 | 0B | 86 | 3E |
| 1870 | B7 | 30 | 0D | 8E | 20 | 00 | 9F | 58 | 3B | 9E | 58 | A6 | 80 | B7 | 30 | 0C |
| 1880 | 9F | 58 | 86 | 36 | B7 | 30 | 0D | 86 | 3F | B7 | 30 | 0D | 3B | 96 | 4A | 26 |
| 1890 | 06 | 86 | 16 | B7 | 30 | 0F | 3B | AD | 9F | 00 | 1C | 20 | 0A | B6 | 38 | 0A |
| 18A0 | 84 | 02 | 26 | 0A | B6 | 38 | 0C | 8A | 80 | AD | 9F | 00 | 18 | 3B | 96 | 47 |
| 18B0 | 26 | 0B | 86 | B5 | B7 | 38 | 0B | 8E | 24 | 00 | 9F | 60 | 3B | 9E | 60 | A6 |
| 18C0 | 80 | B7 | 40 | 0B | 9F | 60 | 3B | 96 | 46 | 26 | 0C | 86 | 35 | B7 | 30 | 0B |
| 18D0 | 8E | 22 | 00 | BF | 22 | 00 | 3B | 9E | 5C | A6 | 80 | B7 | 30 | 0C | 9F | 5C |
| 18E0 | 3B | 96 | 49 | 26 | 06 | 8E | 26 | 00 | 9F | 64 | 3B | 9E | 64 | A6 | 80 | AD |
| 18F0 | 3F | 00 | 26 | 9F | 64 | 3B | 36 | 14 | C6 | 50 | 9E | 3E | D7 | 4B | 9F | 54 |
| 1900 | 0F | 4F | 96 | 4F | 81 | 5E | 26 | FA | 9E | 54 | 9F | 40 | A7 | 01 | 37 | 14 |
| 1910 | 39 | 9E | 50 | D6 | 4B | 81 | 1B | 27 | 21 | 81 | 0D | 26 | 04 | A7 | 82 | 20 |
| 1920 | 1B | 81 | 7F | 26 | 09 | 9C | 3E | 27 | 15 | 30 | 1F | 5C | 20 | 09 | 5D | 27 |
| 1930 | 0D | A7 | 80 | 81 | 3A | 27 | 05 | 5A | 20 | 04 | 30 | 1F | 86 | 5E | 9F | 54 |
| 1940 | D7 | 4B | 3B | B6 | 40 | 0B | 1F | 89 | C4 | 7F | C1 | 10 | 2F | 1D | C1 | 17 |
| 1950 | 2E | 19 | 8E | 80 | 44 | C4 | 07 | C1 | 07 | 26 | 08 | D6 | 44 | 3A | 6F | 84 |

```
1960  0F 44 3B D7 44 3A E7 84 0F 4C 3B 0D 4C 26 41 D6
1970  44 C1 04 27 31 C4 07 27 37 5A 58 58 58 30 8D 00
1980  36 3A 34 02 EC 81 10 AE 81 A7 A4 E7 A4 35 04 4F
1990  5F 10 AE 81 ED A1 10 AE 84 10 9F 50 10 9F 52 10
19A0  AE 84 A7 A4 35 02 97 4C D6 44 C1 04 10 27 FF 61
19B0  9E 50 A7 80 9F 50 3B 00 00 80 4E 80 4B 81 80 3F
19C0  3F 30 0D 80 58 20 00 35 35 30 0B 80 5C 22 00 B5
19D0  BF 38 0B 80 60 24 00 00 00 80 4E 80 4B 81 80 80
19E0  80 80 4D 80 64 26 00 AD 9F F8 0A 17 00 CA 39 86
19F0  03 97 2F 8D 13 0F 3B 17 01 12 17 00 32 20 F0 39
1A00  6E 9F F8 04 6E 9F F8 06 6E 9F F8 0E 6E 9F F8 14
1A10  6E 9F F8 1A 6E 9F F8 1C 6E 9F F8 1E 6E 9F F8 20
1A20  6E 9F F8 22 6E 9F F8 24 39 34 02 86 20 20 57 8D
1A30  4A B6 40 0B 84 7F 81 1B 26 05 32 62 0F 30 39 81
1A40  13 26 F9 03 30 27 F5 8D B7 81 1B 27 ED 81 13 27
1A50  F2 20 F4 4D 26 01 39 4A 34 02 86 0A 17 FF 88 35
1A60  02 20 F0 34 02 0A 3B 2A 10 86 0C 17 FF 79 86 08
1A70  8D E1 86 30 97 3B 17 00 6B 35 82 34 02 8D E4 86
1A80  0D 17 FF 63 86 0A 17 FF 5E 35 82 8D EE 20 02 8D
1A90  9E 34 02 A6 80 81 5E 27 F0 17 FF 4B 20 F5 34 06
1AA0  17 FF 79 17 FF 41 1F 98 17 FF 3C 35 86 9E 3E 34
1AB0  02 B6 40 0A 84 01 35 82 34 04 F6 38 0A C5 02 27
1AC0  F9 B7 38 0B 35 84 39 A6 C0 17 FF D2 A6 C0 16 00
1AD0  2E 17 FF 44 28 02 32 62 39 8D F6 DD 23 8D F2 DD
1AE0  25 9E 23 39 17 FF 48 8D 1D 8D 1B 8D 1B C6 10 96
1AF0  24 84 0F 8D 0A 4C 5A 26 F8 39 17 FF A1 1F 98 17

00 01 02 03 04 05 06 07 08 09 0A 0B 0C 0D 0E 0F
1B00  FF 9C 20 04 20 F4 8D 00 17 FF 1E 39 17 FF CA 29
1B10  FA 17 FF 1B 1F 10 8D EC C6 10 A6 80 17 FF E0 5A
1B20  26 F8 8D E2 C6 10 9E 23 A6 80 2A 04 86 5F 20 08
1B30  81 20 2D F8 81 7F 27 F4 17 FE AC 5A 26 EA 8D 12
1B40  9E 23 8C FF F0 24 C4 30 88 10 9C 25 22 BD 9F 23
1B50  20 BF 96 2F 27 B5 8D 03 4A 20 F9 34 14 C6 64 8E
1B60  00 7C 30 1F 26 FC 5A 26 F6 35 94 17 FF 6B 29 9B
1B70  17 FE BC 9F 33 1F 10 17 FF 80 0F 2E C6 01 A6 84
1B80  84 F0 10 27 00 83 2B 27 81 20 2D 41 27 7B 81 30
1B90  27 51 81 60 2E 72 2D 72 5C A6 01 2A 6D 84 0F 81
1BA0  08 2D 67 27 63 84 0B 81 09 2E 5F 27 5B 20 5A 84
1BB0  B0 81 A0 27 E3 22 51 81 90 27 4E A6 84 84 0F 81
1BC0  03 27 45 81 0C 27 41 81 0E 27 3D 20 3C A6 84 81
1BD0  12 2D 25 81 16 2D 33 81 19 2D 2D 27 2D 81 1D 27
1BE0  29 20 26 A6 84 81 34 2D AF 81 38 2D 1C 81 3C 26
1BF0  19 20 16 A6 80 16 FF 07 8D F9 A6 84 84 F0 81 20
1C00  25 08 10 26 FF 76 C6 01 5C 5C 8D E7 5A 26 FB 17
1C10  FE 1D 17 FF 3D 8C FF FD 24 06 9C 25 10 23 FF 53
1C20  39 17 FE AD 9E 40 9C 3E 27 03 0C 2E 39 32 62 20
1C30  15 17 FE A5 29 3B 0F 2E 9F 33 8D E5 D7 38 8D E1
1C40  D7 39 8D DD D7 3A 17 FD E6 9E 33 10 8E 80 38 96
1C50  2E E6 A0 E1 80 26 0E 4A 26 F7 DC 33 17 FE 9B 17
1C60  FD CD 17 FE ED 9E 33 30 01 27 06 9F 33 9C 25 23
1C70  DA 39 17 FD 9F 81 42 27 01 4F 97 37 39 17 FE 51
1C80  D7 2F 39 17 FE 4B D7 35 39 17 FD 88 81 50 27 01
1C90  4F 97 36 8E 41 00 6F 01 86 FF A7 84 86 3E A7 01
1CA0  A6 84 39 8E 1C CF 17 FD E6 17 FD 83 96 2F 17 FE
1CB0  4E 96 35 17 FE 49 86 50 D6 36 26 02 8B 03 17 FD
1CC0  26 17 FD 65 86 42 0D 37 26 02 86 53 16 FD 18 53
```

```
1CD0  50 20 4E 4C 20 50 20 44 5E 34 04 5F 17 FD 39 29
1CE0  0B E7 9F 80 31 17 FD 41 8D 04 20 F0 35 84 34 06
1CF0  CC 00 01 20 05 34 06 CC FF FF D3 31 DD 31 35 86
1D00  FF FF FF FF FF FF FF FF FF FF FF FF FF FF FF FF
1D10  FF FF FF FF FF FF FF FF FF FF FF FF FF FF FF FF
1D20  FF FF FF FF FF FF FF FF FF FF FF FF FF FF FF FF
1D30  FF FF FF FF FF FF FF FF FF FF FF FF FF FF FF FF
1D40  FF FF FF FF FF FF FF FF FF FF FF FF FF FF FF FF
1D50  FF FF FF FF FF FF FF FF FF FF FF FF FF FF FF FF
1D60  FF FF FF FF FF FF FF FF FF FF FF FF FF FF FF FF
1D70  FF FF FF FF FF FF FF FF FF FF FF FF FF FF FF FF
1D80  FF FF FF FF FF FF FF FF FF FF FF FF FF FF FF FF
1D90  FF FF FF FF FF FF FF FF FF FF FF FF FF FF FF FF
1DA0  FF FF FF FF FF FF FF FF FF FF FF FF FF FF FF FF
1DB0  FF FF FF FF FF FF FF FF FF FF FF FF FF FF FF FF
1DC0  FF FF FF FF FF FF FF FF FF FF FF FF FF FF FF FF
1DD0  FF FF FF FF FF FF FF FF FF FF FF FF FF FF FF FF
1DE0  FF FF FF FF FF FF FF FF FF FF FF FF FF FF FF FF
1DF0  FF FF FF FF FF FF FF FF FF FF FF FF FF FF FF FF 00 01 02 03 04 05 06 07 08 09 0A 0B 0C 0D 0E 0F
1E00  FF FF FF FF FF FF FF FF FF FF FF FF FF FF FF FF
1E10  FF FF FF FF FF FF FF FF FF FF FF FF FF FF FF FF
1E20  FF FF FF FF FF FF FF FF FF FF FF FF FF FF FF FF
1E30  FF FF FF FF FF FF FF FF FF FF FF FF FF FF FF FF
1E40  FF FF FF FF FF FF FF FF FF FF FF FF FF FF FF FF
1E50  FF FF FF FF FF FF FF FF FF FF FF FF FF FF FF FF
1E60  FF FF FF FF FF FF FF FF FF FF FF FF FF FF FF FF
1E70  FF FF FF FF FF FF FF FF FF FF FF FF FF FF FF FF
1E80  FF FF FF FF FF FF FF FF FF FF FF FF FF FF FF FF
1E90  FF FF FF FF FF FF FF FF FF FF FF FF FF FF FF FF
1EA0  FF FF FF FF FF FF FF FF FF FF FF FF FF FF FF FF
1EB0  FF FF FF FF FF FF FF FF FF FF FF FF FF FF FF FF
1EC0  FF FF FF FF FF FF FF FF FF FF FF FF FF FF FF FF
1ED0  FF FF FF FF FF FF FF FF FF FF FF FF FF FF FF FF
1EE0  FF FF FF FF FF FF FF FF FF FF FF FF FF FF FF FF
1EF0  FF FF FF FF FF FF FF FF FF FF FF FF FF FF FF FF
1F00  FF FF FF FF FF FF FF FF FF FF FF FF FF FF FF FF
1F10  FF FF FF FF FF FF FF FF FF FF FF FF FF FF FF FF
1F20  FF FF FF FF FF FF FF FF FF FF FF FF FF FF FF FF
1F30  FF FF FF FF FF FF FF FF FF FF FF FF FF FF FF FF
1F40  FF FF FF FF FF FF FF FF FF FF FF FF FF FF FF FF
1F50  FF FF FF FF FF FF FF FF FF FF FF FF FF FF FF FF
1F60  FF FF FF FF FF FF FF FF FF FF FF FF FF FF FF FF
1F70  FF FF FF FF FF FF FF FF FF FF FF FF FF FF FF FF
1F80  FF FF FF FF FF FF FF FF FF FF FF FF FF FF FF FF
1F90  FF FF FF FF FF FF FF FF FF FF FF FF FF FF FF FF
1FA0  FF FF FF FF FF FF FF FF FF FF FF FF FF FF FF FF
1FB0  FF FF FF FF FF FF FF FF FF FF FF FF FF FF FF FF
1FC0  FF FF FF FF FF FF FF FF FF FF FF FF FF FF FF FF
1FD0  FF FF FF FF FF FF FF FF FF FF FF FF FF FF FF FF
1FE0  FF FF FF FF FF FF FF FF FF FF FF FF FF FF FF FF
1FF0  FF FF FF FF FF FF FF FF FF FF FF FF FF FF FF FF 00 01 02 03 04 05 06 07 08 09 0A 0B 0C 0D 0E 0F
F800  F8 38 F8 93 F8 DC F8 D2 F8 C3 F8 D8 F9 1C F9 0A
F810  F9 16 20 7F F8 E0 F9 2C F9 39 F8 C7 F8 CB F9 8C
F820  F9 79 F9 9B F9 47 FD 97 FF 01 FF 69 FF 79 FF A2
```

```
F830 52 45 56 20 39 2E 30 5E 10 CE 86 FF CE 80 00 8E
F840 F9 CE AF C1 8E F9 D3 AF C1 8E F9 ED AF C1 8E F9
F850 F6 AF C1 86 03 B7 40 0A 86 35 B7 40 0A 8E F9 F6
F860 AF C1 8E FA 24 AF C1 CC 81 00 ED C1 C6 E4 6F C0
F870 5A 26 FB CC FA 0E 8E 80 F4 ED 81 8C 81 00 26 F9
F880 FC 00 00 10 83 59 55 26 04 AD 9F 00 06 30 8C A0
F890 17 00 83 34 FF 86 80 1E 8B 8D 0E 0D 20 27 04 0F
F8A0 20 20 F0 35 7F 32 62 20 EA 7D 40 60 2B 03 7E 08
F8B0 06 8D 33 86 3E 8D 21 8D 12 8E FA C9 17 04 D8 26
F8C0 E8 6E 94 6E 9F 80 04 6E 9F 80 02 0C 21 8D 03 0F
F8D0 21 39 8D 08 81 1B 27 F9 6E 9F 80 06 6E 9F 80 00
F8E0 34 02 86 20 20 2C 8D 22 B6 40 0B 84 7F 81 1B 26
F8F0 05 32 62 0F 2F 39 81 13 26 F9 03 2F 27 F5 8D DC
F900 81 1B 27 ED 81 13 27 F2 20 F4 34 02 86 0D 8D C8
F910 86 0A 8D C4 35 82 8D F2 20 02 8D CA 34 02 A6 80
F920 81 5E 27 F0 8D B2 20 F6 0D 20 2B 08 34 7F 86 80
F930 1E 8B 1F 43 17 01 14 35 FF 34 06 8D 3C 8D 99 1F
F940 98 8D 95 35 86 8D 99 34 14 C6 50 9E 0C 8D 8D 81
F950 1B 27 20 81 0D 26 04 A7 84 20 1A 81 7F 26 09 9C
F960 0C 27 EA 30 1F 5C 20 05 5D 27 E2 A7 80 17 FF 68
F970 5A 20 DA 30 1F 9F 0E 35 94 1F 89 8D 06 1E 89 44
F980 44 44 44 84 0F 8B 90 19 89 40 19 39 0C 21 8D B5
F990 0F 21 81 1B 26 03 1A 02 39 9E 0C 34 20 10 8E 00
F9A0 00 E6 80 4F C0 30 2C 06 1F 20 1C FD 35 A0 C1 09
F9B0 2F 0A C1 11 2D F2 C1 16 2E EE C0 07 34 06 1F 20
F9C0 58 49 58 49 58 49 58 49 E3 E1 1F 02 20 D3 8D 03
F9D0 27 FC 39 8D 18 27 15 B6 40 0B 84 7F 0D 21 27 0A
F9E0 81 5F 23 06 81 7F 27 02 88 20 1C FB 39 34 02 B6
F9F0 40 0A 84 01 35 82 34 04 F6 40 0A C5 02 27 F9 B7
FA00 40 0B 35 84 39 10 AE 6A 86 80 1E 8B 20 17 10 AE
FA10 6A 31 3F 86 80 1E 8B C6 03 8E 80 18 10 AC 83 27
FA20 04 5A 2A F8 3B 10 AF 6A CB 30 17 FE B9 86 23 17
FA30 FE A6 1F 98 17 FE A1 9F 2B 1F 43 8D 0E 9E 2B 0F
FA40 20 17 FE 65 96 20 84 7F 27 F7 3B 8E FA 73 17 FE
FA50 C9 8D 1D 0D 20 2A 02 33 42 34 44 C6 04 8D 3D 5A
FA60 26 FB C6 04 8D 31 5A 26 FB 35 44 1F 40 17 00 A9
FA70 16 FE 73 43 43 20 41 20 20 42 20 20 44 50 20 20
FA80 20 58 20 20 20 20 59 20 20 20 20 55 20 20 20 50
FA90 43 20 20 20 53 50 5E A6 C0 17 FE 9D A6 C0 16 00
FAA0 7D 17 FE E8 28 02 32 62 39 8D F6 DD 22 8D F2 DD
FAB0 24 9E 22 39 20 FD F5 2B FD F9 2D FE 00 3D FE 0B
FAC0 32 FE 13 22 FE 2E 24 FE 3D 41 FB 09 42 FB 23 43
FAD0 FB 57 44 FB 81 46 FB F5 47 FC AB 48 FC CD 49 FD
FAE0 0E 4A FD A4 4B FD AC 4D FD C6 4F FF C7 50 FE 52
FAF0 51 FF 93 52 FE 6A 54 FE BE 56 FF 5F 57 FF 72 58
     00 01 02 03 04 05 06 07 08 09 0A 0B 0C 0D 0E 0F
FB00 FF 0B 5A FF 4C 40 FF 82 00 8D 9E 29 34 8D 6E DC
FB10 22 D3 24 8D 04 DC 22 93 24 17 FE 1D 1F 98 17 FE
FB20 18 20 5A 8D 1D 29 1A 9F 2B 17 FF 75 10 83 00 00
FB30 27 1D 1F 02 A6 A4 9E 2B 10 AF 84 A7 08 86 3F A7
FB40 A4 39 17 FF 5C C1 03 22 06 58 8E 80 10 3A 39 86
FB50 3F 17 FD 84 1A 02 39 17 FF 4F 29 E5 4F 5F 0F 2A
FB60 EB 84 89 00 24 02 0C 2A 9C 24 30 01 25 F2 8D 0D
FB70 34 02 96 2A 17 FD C2 35 02 20 9E 8D 00 17 FD 60
FB80 39 17 FF 25 29 BB 17 FD 5D 8D F0 8D EE 8D EE C6
FB90 10 96 23 84 0F 8D 87 4C 5A 26 F8 17 FD 48 1F 10
```

```
FBA0  8D D7 C6 10 A6 80 17 FF 75 5A 26 F8 8D CD C6 10
FBB0  9E 22 A6 80 2A 04 86 5F 20 08 81 20 2D F8 81 7F
FBC0  27 F4 17 FD 13 5A 26 EA 8D 12 9E 22 8C FF F0 24
FBD0  AF 30 88 10 9C 24 22 A8 9F 22 20 BF 96 2E 27 A0
FBE0  8D 03 4A 20 F9 34 14 C6 64 8E 00 7C 30 1F 26 FC
FBF0  5A 26 F6 35 94 17 FE B1 29 86 17 FC E9 9F 32 1F
FC00  10 17 FF 15 0F 2D C6 01 A6 84 84 F0 10 27 00 83
FC10  2B 27 81 20 2D 41 27 7B 81 30 27 51 81 60 2E 72
FC20  2D 72 5C A6 01 2A 6D 84 0F 81 08 2D 67 27 63 84
FC30  0B 81 09 2E 5F 27 5B 20 5A 84 B0 81 A0 27 E3 22
FC40  51 81 90 27 4E A6 84 84 0F 81 03 27 45 81 0C 27
FC50  41 81 0E 27 3D 20 3C A6 84 81 12 2D 25 81 16 2D
FC60  33 81 19 2D 2D 27 2D 81 1D 27 29 20 26 A6 84 81
FC70  34 2D AF 81 38 2D 1C 81 3C 26 19 20 16 A6 80 16
FC80  FE 9C 8D F9 A6 84 84 F0 81 20 25 08 10 26 FF 76
FC90  C6 01 5C 5C 8D E7 5A 26 FB 17 FC 4A 17 FF 3D 8C
FCA0  FF FD 24 06 9C 24 10 23 FF 53 39 17 FC 1D 81 1B
FCB0  27 0A 0D 20 2A 02 32 62 86 01 97 20 39 17 FD E1
FCC0  9E 0E 9C 0C 27 03 0C 2D 39 32 62 20 15 17 FD D9
FCD0  29 3B 0F 2D 9F 32 8D E5 D7 37 8D E1 D7 38 8D DD
FCE0  D7 39 17 FC 01 9E 32 10 8E 80 37 96 2D E6 A0 E1
FCF0  80 26 0E 4A 26 F7 DC 32 17 FE 1E 17 FB E8 17 FE
FD00  DB 9E 32 30 01 27 06 9F 32 9C 24 23 DA 39 17 FB
FD10  CF 17 FB B7 17 FB C9 8E FD 20 8D 7B 26 43 6E 94
FD20  44 FD 30 53 FD 3B 4E FD 41 50 FD 47 55 F8 38 00
FD30  17 FB 98 81 42 27 01 4F 97 36 39 17 FD 63 D7 2E
FD40  39 17 FD 5D D7 34 39 17 FB 81 81 50 27 01 4F 97
FD50  35 8E 41 00 6F 01 86 FF A7 84 86 3E A7 01 A6 84
FD60  39 8E FD 8D 17 FB B3 17 FB 7C 96 2E 17 FD AF 96
FD70  34 17 FD AA 86 50 D6 35 26 02 8B 03 17 FB 59 17
FD80  FB 5E 86 42 0D 36 26 02 86 53 16 FB 4B 53 50 20
FD90  4E 4C 20 50 20 44 5E A1 80 27 08 30 02 6D 84 26
FDA0  F6 1C FB 39 17 FC FA 1F 01 AD 84 39 34 32 17 FD
FDB0  91 29 11 10 AE 84 6F 84 6F 01 A6 A4 81 3F 26 04
FDC0  A6 08 A7 A4 35 B2 17 FC D8 DD 30 17 FB 18 DC 30
FDD0  17 FD 46 A6 9F 80 30 17 FD 44 17 FA EE 81 0D 27
FDE0  C2 17 FA FC 8E FA B4 8D AE 26 E0 86 80 97 20 AD
FDF0  94 0F 20 20 D6 8D 14 29 19 34 06 CC 00 01 20 05

00 01 02 03 04 05 06 07 08 09 0A 0B 0C 0D 0E 0F
FE00  34 06 CC FF FF D3 30 DD 30 35 86 17 FC 93 E7 9F
FE10  80 30 39 E6 9F 80 30 8D 03 17 FA C4 34 10 8E 00
FE20  04 86 18 58 49 17 FA B0 30 1F 26 F5 35 90 17 FA
FE30  A1 81 0D 27 DD A7 9F 80 30 8D BE 20 F1 34 04 5F
FE40  17 FB 49 29 0B E7 9F 80 30 17 FA 94 8D AB 20 F0
FE50  35 84 86 03 8E 80 18 17 FA B0 17 FC C1 34 02 EC
FE60  83 17 FC B5 35 02 4A 2A EE 39 33 62 17 FB DC 17
FE70  FA 59 81 0D 27 36 8E FE AD A1 81 27 08 6D 84 10
FE80  27 FC CC 20 F4 A6 82 34 02 17 FB 00 28 02 35 82
FE90  1F 02 35 04 C1 0A 26 08 1E 24 86 01 97 20 6E B4
FEA0  33 C5 C5 0C 1F 20 27 02 A7 C0 E7 C4 39 43 00 41
FEB0  01 42 02 44 03 58 04 59 06 55 08 53 0A 00 17 FB
FEC0  E8 29 E9 5F 20 29 9E 22 8D 2E A7 80 9C 24 23 F8
FED0  9E 22 8D 24 A3 84 10 26 FA 4E 30 01 9C 24 23 F2
FEE0  86 23 17 F9 F3 17 FA 00 5C 27 C1 0A 2C 26 D7 17
FEF0  F9 F4 86 40 97 2C 20 CE 9F 2A 1F 98 9B 2A 9B 2B
FF00  39 34 3A 86 80 1E 8B 8D 0C 35 BA 17 FB 9B 29 3B
```

```
FF10  17 FB 8E DD 26 10 9E 26 9E 22 10 9C 22 27 2C 25
FF20  05 10 9C 24 25 0F A6 80 A7 A0 8C 00 00 27 1C 9C
FF30  24 23 F3 20 16 1F 20 93 22 D3 24 1F 02 9E 24 A6
FF40  84 A7 A4 30 1F 31 3F 9C 22 26 F4 39 17 FB 5A 29
FF50  0D 17 FA 38 29 08 9E 22 E7 80 9C 24 23 FA 39 17
FF60  FA 2A 29 FA 8D 03 16 FB B5 CA 80 F7 40 A0 B6 40
FF70  40 39 17 FB 34 96 23 D6 25 C4 7F B7 40 80 F7 40
FF80  A0 39 17 FA 07 29 D7 1F 01 86 3D 17 F9 4A A6 80
FF90  16 F9 A6 86 3D 17 F9 40 8D 08 17 F9 9C 1E 89 16
FFA0  F9 97 86 80 B5 40 C0 27 FB B5 40 C0 26 FB B6 40
FFB0  21 F6 40 22 97 3A 84 8F 88 80 2A 08 84 0F DD 3B
FFC0  4F 5F 93 3B 09 3A 39 17 FA DF E7 80 39 6E 9F 80
FFD0  F4 6E 9F 80 FA 6E 9F 80 F8 6E 9F 80 F6 6E 9F 80
FFE0  FC FF FF FF FF FF FF FF FF FF FF FF FF FF FF FF
FFF0  F8 93 FF D1 FF D5 FF DD FF CD FF D9 FA 05 F8 38
```

The embodiments of the invention in which an exclusive property or privilege is claimed are as follows:

1. A computer-aided chemical analyzer for analysis of physiological samples, comprising:
   (a) means for holding a test sample at a sample station;
   (b) means for performing a plurality of analytical tests of said test sample, said analytical testing means further comprising a plurality of input/output devices for providing output signals representative of physical characteristics of the test sample, and said input/output devices including a monochromatic scanning spectrophotometer for selectively directing substantially monochromatic light of a selected wavelength at a test sample and means for measuring the monochromatic light absorbed by the test sample;
   (c) processing means including a host digital computer having a control program for controlling the analytical testing means and calculating data from output signals of the input/output devices; and
   (d) computer compatible data entry means for communicating specific test instructions to said processing means, wherein said data entry means may provide test instructions to operate and control at least one of the input/output devices, and wherein said control program includes primitive instructions designed to utilize test instructions received by said computer compatible data entry means to automatically create new control and test procedures and parameters for performing and controlling analysis of a test sample with one or more of said input/output devices.

2. The computer-aided chemical analyzer of claim 1, wherein additional input/output devices can be added to said analytic testing means as desired.

3. The computer-aided chemical analyzer of claim 1, wherein said primitive instructions may be combined with other commands to create more complex instructions for carrying out a particular test.

4. The computer-aided chemical analyzer of claim 1, wherein the primitive instructions of said control program remain unchanged by test instructions received by said data entry means and by the creation of the new control and test procedures and parameters initiated by said test.

5. A computer-aided chemical analyzer as recited in claim 1 further including a plurality of ion selective electrodes, each of said electrodes having an output in selective communication with the processing means, wherein the processing means can perform calculations with data from selective of the electrode outputs in accordance with the specific test instructions communicated from the data entry means.

6. A computer-aided chemical analyzer as recited in claim 1 further including means for interrogating selective outputs of the input/output devices and applying the interrogated outputs to the processing means.

7. A computer-aided chemical analyzer as recited in claim 1 further including timing means for establishing a time duration for a predetermined response of one or more of the input/output device outputs.

8. A computer-aided chemical analyzer as recited in claim 1, wherein the computer compatible data entry means includes means for reading an optical bar code.

* * * * *